(12) United States Patent
Nematihosseinabadi et al.

(10) Patent No.: US 11,380,351 B2
(45) Date of Patent: Jul. 5, 2022

(54) SYSTEM AND METHOD FOR PULMONARY CONDITION MONITORING AND ANALYSIS

(71) Applicant: Samsung Electronics Co., Ltd., Suwon-si (KR)

(72) Inventors: Ebrahim Nematihosseinabadi, Santa Clara, CA (US); Md Mahbubur Rahman, San Jose, CA (US); Viswam Nathan, Mountain View, CA (US); Korosh Vatanparvar, Santa Clara, CA (US); Jilong Kuang, San Jose, CA (US); Jun Gao, Menlo Park, CA (US)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 135 days.

(21) Appl. No.: 16/247,384

(22) Filed: Jan. 14, 2019

(65) Prior Publication Data

US 2020/0098384 A1    Mar. 26, 2020

Related U.S. Application Data

(60) Provisional application No. 62/733,911, filed on Sep. 20, 2018.

(51) Int. Cl.
*G10L 25/66* (2013.01)
*G10L 15/06* (2013.01)
(Continued)

(52) U.S. Cl.
CPC ............ *G10L 25/66* (2013.01); *A61B 5/0823* (2013.01); *A61B 5/4803* (2013.01); *A61B 5/7267* (2013.01); *G10L 15/02* (2013.01); *G10L 15/063* (2013.01); *G10L 15/22* (2013.01); *G10L 2015/0635* (2013.01); *G10L 2015/226* (2013.01)

(58) Field of Classification Search
None
See application file for complete search history.

(56) References Cited

U.S. PATENT DOCUMENTS 6,055,499 A * 4/2000 Chengalvarayan ..... G10L 15/02
    704/207
6,289,313 B1    9/2001 Heinonen et al.
(Continued)

FOREIGN PATENT DOCUMENTS

WO    2013057637 A1    4/2013
WO    2016028495 A1    2/2016

OTHER PUBLICATIONS

M. Farrús, J. Hernando, and P. Ejarque, "Jitter and Shimmer Measurements for Speaker Recognition," Eurospeech, Antwerp, Belgium, 2007. https://www.cs.upc.edu/~nlp/papers/far_jit_07.pdf. 2007.*

(Continued)

*Primary Examiner* — Fariba Sirjani
(74) *Attorney, Agent, or Firm* — Sherman IP LLP; Kenneth L. Sherman; Steven Laut

(57) ABSTRACT

A method for pulmonary condition monitoring includes selecting a phrase from an utterance of a user of an electronic device, wherein the phrase matches an entry of multiple phrases. At least one speech feature that is associated with one or more pulmonary conditions within the phrase is identified. A pulmonary condition is determined based on analysis of the at least one speech feature.

20 Claims, 14 Drawing Sheets

(51) Int. Cl.
*G10L 15/22* (2006.01)
*G10L 15/02* (2006.01)
*A61B 5/08* (2006.01)
*A61B 5/00* (2006.01)

(56) References Cited

U.S. PATENT DOCUMENTS

| | | | | |
|---|---|---|---|---|
| 7,529,670 | B1* | 5/2009 | Michaelis | A61B 5/091 381/84 |
| 9,070,367 | B1* | 6/2015 | Hoffmeister | G10L 15/063 |
| 9,685,174 | B2* | 6/2017 | Karam | A61B 5/7267 |
| 10,028,675 | B2* | 7/2018 | Patel | A61B 5/0871 |
| 10,799,186 | B2* | 10/2020 | Howard | G16H 70/60 |
| 2002/0139842 | A1* | 10/2002 | Swaine | G06Q 20/18 235/379 |
| 2009/0313019 | A1* | 12/2009 | Kato | G10L 17/26 704/254 |
| 2010/0298649 | A1 | 11/2010 | Warkentin et al. | |
| 2011/0184250 | A1* | 7/2011 | Schmidt | G16H 50/50 600/300 |
| 2012/0116186 | A1* | 5/2012 | Shrivastav | A61B 5/4803 600/301 |
| 2012/0265024 | A1* | 10/2012 | Shrivastav | A61B 5/165 600/300 |
| 2014/0276228 | A1* | 9/2014 | De Waele | A61B 5/1075 600/586 |
| 2015/0073306 | A1* | 3/2015 | Abeyratne | G06K 9/00523 600/586 |
| 2015/0112232 | A1* | 4/2015 | Quatieri | A61B 5/7264 600/595 |
| 2015/0318002 | A1* | 11/2015 | Karam | G10L 25/48 704/231 |
| 2015/0364146 | A1* | 12/2015 | Larsen | G10L 21/14 704/276 |
| 2017/0231528 | A1* | 8/2017 | Nathan | A61B 5/4806 600/483 |
| 2017/0251985 | A1* | 9/2017 | Howard | A61B 5/165 |
| 2017/0367676 | A1 | 12/2017 | Mac et al. | |
| 2018/0184963 | A1 | 7/2018 | Levanon | |
| 2018/0214061 | A1* | 8/2018 | Knoth | A61B 5/165 |
| 2018/0240535 | A1* | 8/2018 | Harper | G16H 50/30 |
| 2018/0254041 | A1* | 9/2018 | Harper | G10L 25/51 |
| 2018/0322961 | A1* | 11/2018 | Kim | G06N 3/08 |
| 2019/0080803 | A1* | 3/2019 | Lotan | A61B 5/4803 |
| 2019/0362740 | A1* | 11/2019 | Hauptman | G10L 25/66 |
| 2020/0037942 | A1* | 2/2020 | Howard | A61B 5/112 |
| 2020/0075040 | A1* | 3/2020 | Provost | G06N 3/08 |
| 2020/0098384 | A1* | 3/2020 | Nematihosseinabadi | G10L 15/22 |

OTHER PUBLICATIONS

Sun, X., et al., "SymDetector: detecting sound-related respiratory symptoms using smartphones", In Proceedings of the 2015 ACM International Joint Conference on Pervasive and Ubiquitous Computing, Sep. 2015, pp. 97-108. ACM, United States.
Hoit, J.D.. et al, "Nature and evaluation of dyspnea in speaking and swallowing," In Seminars in speech and language, Feb. 2011, vol. 32, No. 01, pp. 005-020, © Thieme Medical Publishers, Stuttgart [Abstract Only].
Wiechern, B., et al., "Effects of asthma on breathing during reading aloud", Speech, Language and Hearing, 21(1), 2018, pp. 30-40, Taylor & Francis Online, United Kingdom [Abstract Only].
Rabiner, L.R., "A tutorial on hidden Markov models and selected applications in speech recognition." Proceedings of the IEEE, 1989, pp. 257-286, No. 2, IEEE, United States.
Bilmes, J. A. "Graphical models and automatic speech recognition." In Mathematical foundations of speech and language processing, 2004, pp. 191-245. Springer, New York, NY.
Hinton, G. et al. "Deep neural networks for acoustic modeling in speech recognition: The shared views of four research groups." IEEE Signal processing magazine, 2012, pp. 82-97, vol. 29, No. 6, IEEE, United States.
Saeed, A. et al., "Study of voice disorders in patients with bronchial asthma and chronic obstructive pulmonary disease," Egyptian Journal of Bronchology, 2018, vol. 12, No. 01, pp. 020-026, Cairo, Egypt.
Umapahy, K et al., Discrimination of pathological voices using a time-frequency approach. IEEE Transactions on Biomedical Engineering, 2005, 52(3), pp. 421-430, IEEE, United States, [Abstract Only].
Garofolo, J.S., et al., "TIMIT Acoustic-Phonetic Continuous Speech Corpus," LDC93S1. CD-ROM. University of Philadelphia: Linguistic Data Consortium, 2002, {Abstract Only}.
Fraley, R. C. et al., "Review of intensive longitudinal methods: an introduction to diary and experience sampling research." Journal of Social Psychology, 2014, pp. 89-91, vol. 154, issue 1, Taylor & Francis Online, United Kingdom [Abstract Only].
Keppenne, C.L. et al., "Data assimilation into a primitive-equation model with a parallel ensemble Kalman filter", Monthly Weather Review, Jun. 2000, pp. 1971-1981, vol. 128, American Meteorological Society, United States.
McGraw, I. et al. "Personalized speech recognition on mobile devices", arXiv preprint arXiv:1603.03185, Mar. 11, 2016, pp. 1-5, United States.
Basso, M. et al., "NARX models of an industrial power plant gas turbine", IEEE Transactions on control systems technology, 2004, pp. 599-604, 13, No. 4, IEEE, United States.
Connor, J.T. et al., "Recurrent neural networks and robust time series prediction", IEEE transactions on neural networks, Mar. 1994, pp. 240-254, v. 5, No. 2, IEEE, United States.
International Search Report and Written Opinion dated Dec. 27, 2019 for International Application PCT/KR2019/012240 from Korean Intellectual Property Office, pp. 1-8, Republic of Korea.
Nathan, V., et al., "Assessment of Chronic Pulmonary Disease Patients Using Biomarkers from Natural Speech Recorded by Mobile Devices," 2019 IEEE 16th International Conference on Wearable and Implantable Body Sensor Networks (BSN), May 19, 2019, pp. 1-4, IEEE United States.
Shastry, A., et al., "Voice Analysis in Individuals with Chronic Obstructive Pulmonary Disease" International Journal of Phonosurgery & Laryngology, vol. 4, No. 2, Jul. 1, 2014, pp. 45-49, Manipal Academy of Higher Education.
Extended European Search Report dated Oct. 19, 2021 for European Application No. 19862458.7 from European Patent Office. pp. 1-12, Munich, Germany.

* cited by examiner

SYSTEM AND METHOD FOR PULMONARY CONDITION MONITORING AND ANALYSIS

CROSS-REFERENCE TO RELATED APPLICATIONS

This application claims the priority benefit of U.S. Provisional Patent Application No. 62/733,911, filed on Sep. 20, 2018, which is incorporated herein by reference in its entirety.

COPYRIGHT DISCLAIMER

A portion of the disclosure of this patent document may contain material that is subject to copyright protection. The copyright owner has no objection to the facsimile reproduction by anyone of the patent document or the patent disclosure as it appears in the patent and trademark office patent file or records, but otherwise reserves all copyright rights whatsoever.

TECHNICAL FIELD

One or more embodiments generally relate to health monitoring, in particular, to pulmonary condition monitoring involving a voice assistant.

BACKGROUND

Currently, the number of adults with chronic obstructive pulmonary disease (COPD) in the United States is over 12 million. This number goes up to 25 million when it comes to joining those with Asthma. Continuously monitoring these patients is perhaps a critical approach to predict and prevent acute exacerbation events. These events, if not treated in time, can lead to lengthy hospitalization and mortality. In general, the cost of treating pulmonary diseases in the United States is about $154 billion per year with a 6% increase every year. Early detection of lung worsening for chronic pulmonary patients would greatly reduce hospital readmissions, improve patient outcomes and their quality of life. Audio-based remote monitoring of patients seems to be one inexpensive and effective method for detecting symptoms such as coughing, speech pattern changes, shortness of breath, etc. While continuous recording of audio can help in detection and analysis of these symptoms, it comes with a couple of major issues: 1—privacy of the user; 2—inconsistency of the data which makes detecting changes in speech pattern recognition very difficult; 3—limitation of the resources on mobile devices such as battery, processing power and memory; and 4—interference of audio noise sources such as environmental noise with target symptom sounds which makes in-field passive sensing very challenging.

SUMMARY

One or more embodiments generally relate to health condition monitoring. In one embodiment, a method for pulmonary condition monitoring includes selecting a phrase from an utterance of a user of an electronic device, wherein the phrase matches an entry of multiple phrases. At least one speech feature that is associated with one or more pulmonary conditions within the phrase is identified. A pulmonary condition is determined based on analysis of the at least one speech feature.

In some embodiments, an electronic device includes a memory storing instructions. At least one processor executes the instructions including a process configured to select a phrase from an utterance of a user of the electronic device, wherein the phrase matches an entry of a plurality of phrases; identify at least one speech feature that is associated with one or more pulmonary conditions within the phrase; and determine a pulmonary condition based on analysis of the at least one speech feature.

In one or more embodiments, a non-transitory processor-readable medium that includes a program that when executed by a processor performing a method that includes selecting a phrase from an utterance of a user of an electronic device, wherein the phrase matches an entry of multiple phrases. At least one speech feature that is associated with one or more pulmonary conditions within the phrase is identified. A pulmonary condition is determined based on analysis of the at least one speech feature.

These and other aspects and advantages of one or more embodiments will become apparent from the following detailed description, which, when taken in conjunction with the drawings, illustrate by way of example the principles of the one or more embodiments.

BRIEF DESCRIPTION OF THE DRAWINGS

For a fuller understanding of the nature and advantages of the embodiments, as well as a preferred mode of use, reference should be made to the following detailed description read in conjunction with the accompanying drawings, in which.

DETAILED DESCRIPTION

Figure 1:
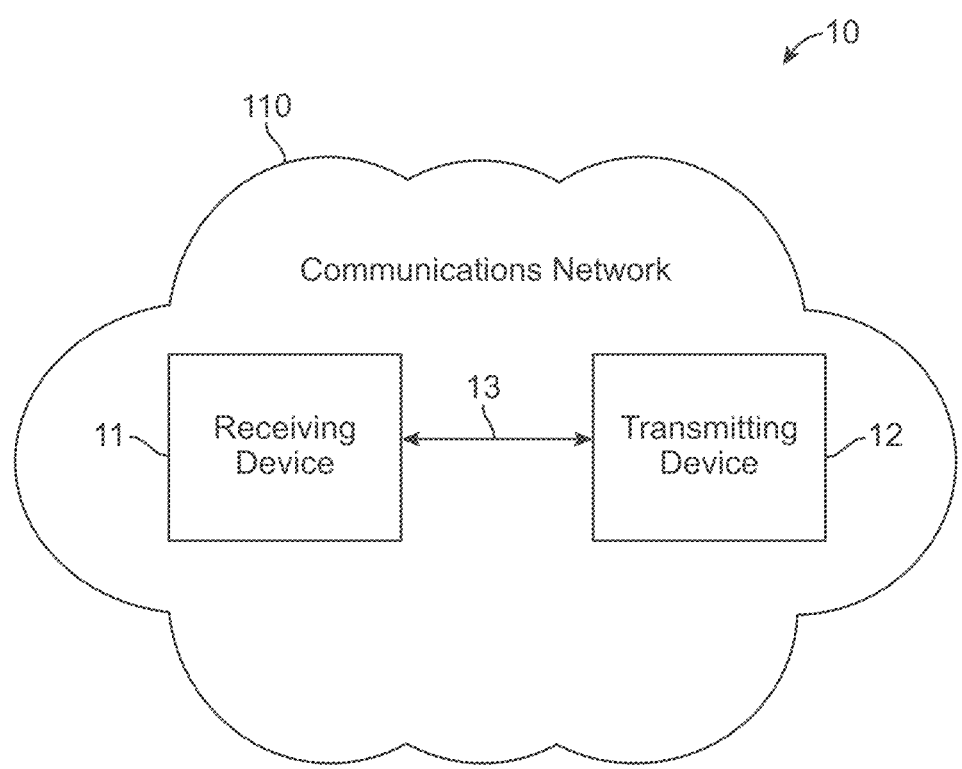
FIG. 1 shows a schematic view of a communications system, according to some embodiments.

The following description is made for the purpose of illustrating the general principles of one or more embodiments and is not meant to limit the inventive concepts claimed herein. Further, particular features described herein can be used in combination with other described features in each of the various possible combinations and permutations. Unless otherwise specifically defined herein, all terms are to be given their broadest possible interpretation including meanings implied from the specification as well as meanings understood by those skilled in the art and/or as defined in dictionaries, treatises, etc.

It should be noted that the terms "at least one of" refers to one or more than one of the elements that follow. For example, "at least one of a, b, c, or a combination thereof" may be interpreted as "a," "b," or "c" individually; or as "a" and "b" together in combination, as "b" and "c" together in combination; as "a" and "c" together in combination; or as "a," "b" and "c" together in combination.

One or more embodiments provide for pulmonary condition monitoring. Some embodiments include a method that includes selecting a phrase from an utterance of a user of an electronic device, wherein the phrase matches an entry of multiple phrases. At least one speech feature that is associated with one or more pulmonary conditions within the phrase is identified. A pulmonary condition is determined based on analysis of the at least one speech feature.

Some embodiments take advantage of a voice assistant (e.g., personal assistant (PA), virtual assistant, etc.), employing features, such as recorded speech, usage information and contextual data to generate a sparse but private and consistent data source for semi-continuous monitoring of patients (such as pulmonary patients, etc.). Data mining and machine learning processing are employed to analyze theses sources of data and track the changes for health symptoms and alert the patient and caregiver when needed. In one or more embodiments, audio commands that are used to communicate and interact with voice assistants are used as a resource for assessment of health status of the patient, and prediction of, for example, pulmonary-related deadly events such as asthma attack and COPD exacerbation. Voice assistants provide a unique source of data. In some embodiments, the processing for "phrase spotting" selects specific phrases based on an initial criterion and the feedback that is retrieved from longitudinal analysis of patient status. These selected phrases are used as the sources for speech feature generation and data analysis. The characteristics of vowels, pause patterns and syllable segments in these selected phrases are stored (e.g., in a phrase bank, knowledge base, etc.) and are used to generate a model for location of interesting parts of the phrase. The model continuously updates itself when receiving the same phrase over and over. Having a consistent continuous stream of these phrases ensures that this model converges to a consistent state for each subject (i.e., a user of an electronic device, a pulmonary patient, etc.), thus realizing a personalized model.

In some embodiments, a model for location continuously updates itself using an online learning scheme. The continuously updating model is also utilized for detecting vowels, pause patterns and syllable segments of the audio, which then is fed to speech feature generation processing. These features are then fed to longitudinal analysis processing where patient status deviation is estimated. If these variations in the patient's status appear to be alarming, a notification will be sent to the clinician, and if necessary, clinicians will intervene any probable dangerous health-related events. In one or more embodiments, some of the issues of passive audio collection are resolved: voice assistant audio data is not privacy-sensitive in comparison to passive audio data that is continuously recorded. It is an audio data that the subject is willing to release and the contents are usually multitude of voice commands, which are not private and sensitive material. The passively recorded audio data comes with a variety of speech phrases and words. However, the proportion of consistent, repeated phrases is much lower when compared to the set of voice assistant audio commands. Therefore, tracking speech feature deviation is easier when it comes to voice assistant audio data. Running a passive continuous audio collection can also be relatively high demand in terms of battery lifetime, processing and data storage. On the other hand, if voice assistant data is utilized, only a limited set of smartly selected phrases are needed. Moreover, collection of information about some specific parts of the audio, the entire audio stream is not required to be collected. It is noted that voice assistant audio data is not privacy-sensitive in comparison to passive audio recorded data. Voice assistant audio includes audio data that a subject is willing to release and the contents are usually some voice command, which is not private and sensitive material. Unlike conventional systems, one or more embodiments take advantage of the fact that users are already giving consent for the recording of the voice for voice assistants. Therefore, no additional permission for recording is needed (e.g., reliance on the recording of existing voice commands instead of recording patients all the time).

Another big challenge of passive audio collection is dealing with a variety of different audio noise sources. These can increase the false positives and false negatives when it comes to detecting symptoms and features of speech. Interactions with a voice assistant on the other hand are not generally hampered by this issue. The reason is that in order to talk to a voice assistant, the user instinctively makes sure there is no interference when he or she is communicating with it (e.g., muting television audio, etc.). The user also automatically makes sure to be close enough to the voice assistant when saying a command. Some embodiments have the advantage of being cross-platform and pervasive: they are not limited to a specific device; any device equipped with a voice assistant can be used.

Some embodiments utilize existing platforms, such as a personal assistant (e.g., SAMSUNG's® Bixby) or a smartphone to develop a new service, for example pulmonary patient monitoring. Health monitoring processing defines a new source of data stream for pulmonary applications using the existing platforms. In some embodiments, phrase spotting is implemented for detection and analysis of a selective set of phrases relevant to, for example, pulmonary health estimation, rather than the whole speech. In one or more embodiments, health monitoring processing continuously updates the model using the result of longitudinal analysis of patient status.

Some embodiments perform analysis on a consistent, more standard audio input data rather than whole speech, which makes the detection of feature deviation more valuable and trustworthy. The voice assistant has less limitations in terms of battery, storage and processing compared to continuous audio recording. Many devices that use voice assistants are not portable. Therefore, in one or more embodiments a lot of the processing is performed on the device instead of a server or cloud environment which makes the sensing more robust and secure.

FIG. 1 is a schematic view of a communications system 10, in accordance with one embodiment. Communications system 10 may include a communications device that initiates an outgoing communications operation (transmitting device 12) and a communications network 110, which transmitting device 12 may use to initiate and conduct communications operations with other communications devices within communications network 110. For example, communications system 10 may include a communication device that receives the communications operation from the transmitting device 12 (receiving device 11). Although communications system 10 may include multiple transmitting devices 12 and receiving devices 11, only one of each is shown in FIG. 1 to simplify the drawing.

Any suitable circuitry, device, system or combination of these (e.g., a wireless communications infrastructure including communications towers and telecommunications servers) operative to create a communications network may be used to create communications network 110. Communications network 110 may be capable of providing communications using any suitable communications protocol. In some embodiments, communications network 110 may support, for example, traditional telephone lines, cable television, Wi-Fi (e.g., an IEEE 802.11 protocol), BLUETOOTH® high frequency systems (e.g., 900 MHz, 2.4 GHz, and 5.6 GHz communication systems), infrared, other relatively localized wireless communication 33protocol, or any combination thereof. In some embodiments, the communications network 110 may support protocols used by wireless and cellular phones and personal email devices (e.g., a BLACKBERRY®). Such protocols may include, for example, GSM, GSM plus EDGE, CDMA, quadband, and other cellular protocols. In another example, a long-range communications protocol can include Wi-Fi and protocols for placing or receiving calls using VOIP, LAN, WAN, or other TCP-IP based communication protocols. The transmitting device 12 and receiving device 11, when located within communications network 110, may communicate over a bidirectional communication path such as path 13, or over two unidirectional communication paths. Both the transmitting device 12 and receiving device 11 may be capable of initiating a communications operation and receiving an initiated communications operation.

The transmitting device 12 and receiving device 11 may include any suitable device for sending and receiving communications operations. For example, the transmitting device 12 and receiving device 11 may include, but are not limited to devices including a voice assistant (personal assistant, virtual assistant, etc.) such as mobile telephone devices, television (TV) systems, smart TV systems, cameras, camcorders, a device with audio video capabilities, tablets, wearable devices, smart appliances, smart picture frames, and any other device capable of communicating wirelessly (with or without the aid of a wireless-enabling accessory system) or via wired pathways (e.g., using traditional telephone wires). The communications operations may include any suitable form of communications, including for example, voice communications (e.g., telephone calls), data communications (e.g., data and control messaging, e-mails, text messages, media messages), video communication, or combinations of these (e.g., video conferences).

Figure 2:
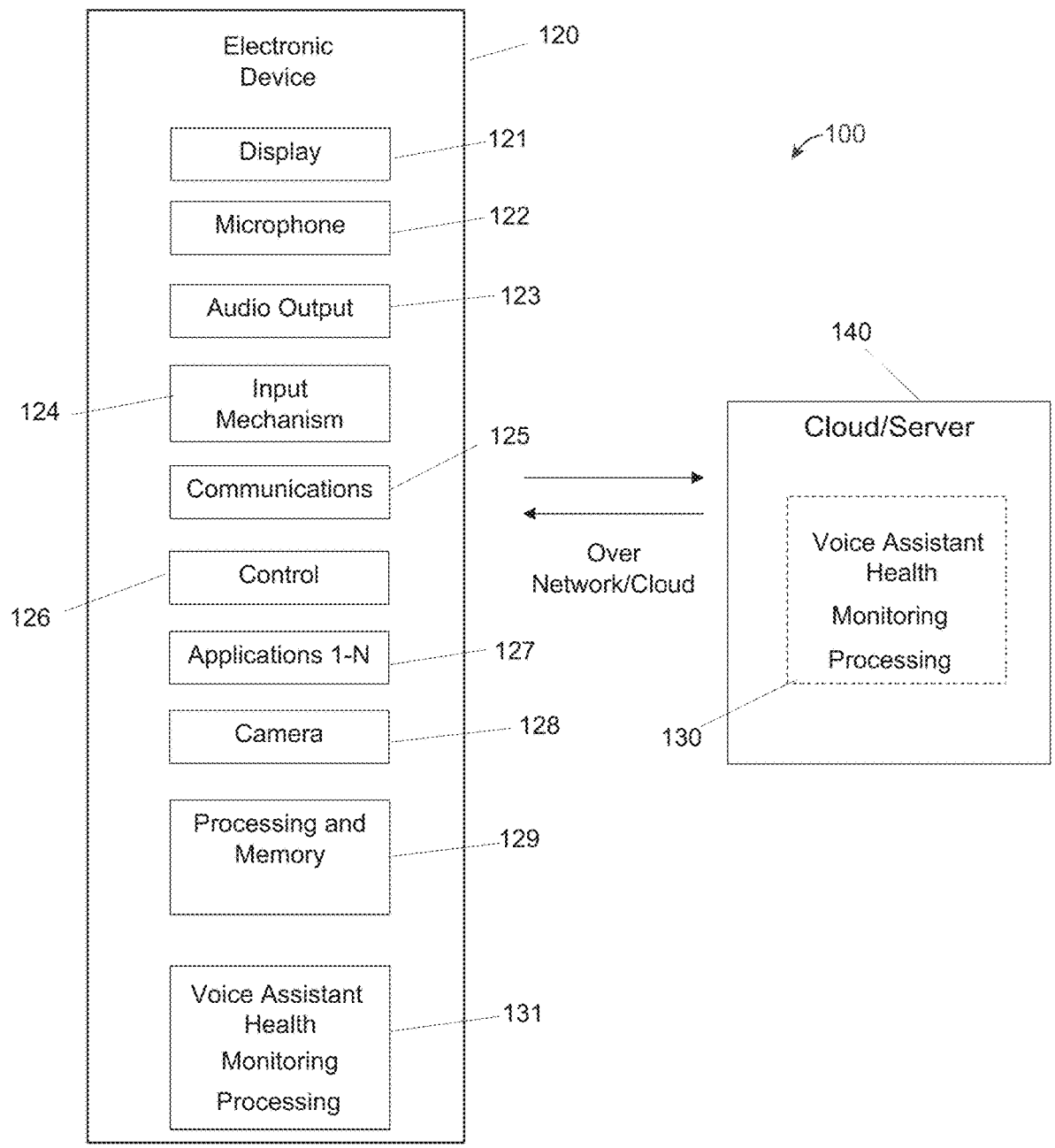
FIG. 2 shows a block diagram of architecture for a system including an electronic device and a cloud or server environment, that is capable of performing individually or in combination, voice assistant health monitoring processing, according to some embodiments.

FIG. 2 shows a block diagram of an architecture for a system 100 that is capable of performing health condition (e.g., pulmonary condition) monitoring using an electronic device 120 (e.g., mobile telephone devices, TV systems, cameras, camcorders, a device with audio video capabilities, tablets, pad devices, wearable devices, smart appliances, smart picture frames, smart lighting, etc.), a cloud or server 140, or a combination of the electronic device 120 and the cloud computing (e.g., shared pools of configurable computing system resources and higher-level services, etc.) or server (e.g., a computer, device, or program that manages network resources, etc.) 140. Both the transmitting device 12 (FIG. 1) and receiving device 11 may include some or all of the features of the electronics device 120. In some embodiments, the electronic device 120 may comprise a display 121, a microphone 122, an audio output 123, an input mechanism 124, communications circuitry 125, control circuitry 126, a camera 128, processing and memory 129, voice assistant health (e.g., pulmonary, etc.) monitoring processing 130 and/or 131 (for processing on the electronic device 120, on the cloud/server 140, on a combination of the electronic device 120 and the cloud/server 140, communicating with the communications circuitry 125 to obtain/provide information thereof with the cloud or server 140; and may include any of the processing for, but not limited to, the examples as described below, and any other suitable components. Applications 1-N 127 are provided and may be obtained from a cloud or server 140, a communications network 110, (FIG. 1) etc., where N is a positive integer equal to or greater than 1.

In some embodiments, all of the applications employed by the audio output 123, the display 121, input mechanism 124, communications circuitry 125, and the microphone 122 may be interconnected and managed by control circuitry 126. In one example, a handheld music player capable of transmitting music to other tuning devices may be incorporated into the electronics device 120.

In some embodiments, the audio output 123 may include any suitable audio component for providing audio to the user of electronics device 120. For example, audio output 123 may include one or more speakers (e.g., mono or stereo speakers) built into the electronics device 120. In some embodiments, the audio output 123 may include an audio component that is remotely coupled to the electronics device 120. For example, the audio output 123 may include a headset, headphones, or earbuds that may be coupled to communications device with a wire (e.g., coupled to electronics device 120 with a jack) or wirelessly (e.g., BLUETOOTH® headphones or a BLUETOOTH® headset).

In some embodiments, the display 121 may include any suitable screen or projection system for providing a display visible to the user. For example, display 121 may include a screen (e.g., an LCD screen, LED screen, OLED screen, etc.) that is incorporated in the electronics device 120. As another example, display 121 may include a movable display or a projecting system for providing a display of content on a surface remote from electronics device 120 (e.g., a video projector). Display 121 may be operative to display content (e.g., information regarding communications operations or information regarding available media selections) under the direction of control circuitry 126.

In some embodiments, input mechanism 124 may be any suitable mechanism or user interface for providing user inputs or instructions to electronics device 120. Input mechanism 124 may take a variety of forms, such as a button, keypad, dial, a click wheel, mouse, visual pointer, remote control, one or more sensors (e.g., a camera or visual sensor, a light sensor, a proximity sensor, etc., or a touch screen. The input mechanism 124 may include a multi-touch screen.

In some embodiments, communications circuitry 125 may be any suitable communications circuitry operative to connect to a communications network (e.g., communications network 110, FIG. 1) and to transmit communications operations and media from the electronics device 120 to other devices within the communications network. Communications circuitry 125 may be operative to interface with the communications network using any suitable communications protocol such as, for example, Wi-Fi (e.g., an IEEE 802.11 protocol), Bluetooth®, high frequency systems (e.g., 900 MHz, 2.4 GHz, and 5.6 GHz communication systems), infrared, GSM, GSM plus EDGE, CDMA, quadband, and other cellular protocols, VOIP, TCP-IP, or any other suitable protocol.

In some embodiments, communications circuitry 125 may be operative to create a communications network using any suitable communications protocol. For example, communications circuitry 125 may create a short-range communications network using a short-range communications protocol to connect to other communications devices. For example, communications circuitry 125 may be operative to create a local communications network using the BLUETOOTH® protocol to couple the electronics device 120 with a BLUETOOTH® headset.

In some embodiments, control circuitry 126 may be operative to control the operations and performance of the electronics device 120. Control circuitry 126 may include, for example, a processor, a bus (e.g., for sending instructions to the other components of the electronics device 120), memory, storage, or any other suitable component for controlling the operations of the electronics device 120. In some embodiments, one or more processors (e.g., in processing and memory 129) may drive the display and process inputs received from the user interface. The memory and storage may include, for example, cache, Flash memory, ROM, and/or RAM/DRAM. In some embodiments, memory may be specifically dedicated to storing firmware (e.g., for device applications such as an operating system, user interface functions, and processor functions). In some embodiments, memory may be operative to store information related to other devices with which the electronics device 120 performs communications operations (e.g., saving contact information related to communications operations or storing information related to different media types and media items selected by the user).

In some embodiments, the control circuitry 126 may be operative to perform the operations of one or more applications implemented on the electronics device 120. Any suitable number or type of applications may be implemented. Although the following discussion will enumerate different applications, it will be understood that some or all of the applications may be combined into one or more applications. For example, the electronics device 120 may include applications 1-N 127 including, but not limited to: an automatic speech recognition (ASR) application, OCR application, a dialog application, a map application, a media application (e.g., QuickTime, MobileMusic.app, or MobileVideo.app), social networking applications (e.g., FACEBOOK®, INSTAGRAM®, TWITTER®, etc.), a calendaring application (e.g., a calendar for managing events, appointments, etc.), an Internet browsing application, a recommender application, etc. In some embodiments, the electronics device 120 may include one or multiple applications operative to perform communications operations. For example, the electronics device 120 may include a messaging application, an e-mail application, a voicemail application, an instant messaging application (e.g., for chatting), a videoconferencing application, a fax application, or any other suitable application for performing any suitable communications operation.

In some embodiments, the electronics device 120 may include a microphone 122. For example, electronics device 120 may include microphone 122 to allow the user to transmit audio (e.g., voice audio) for speech control and navigation of applications 1-N 127, during a communications operation or as a means of establishing a communications operation or as an alternative to using a physical user interface. The microphone 122 may be incorporated in the electronics device 120, or may be remotely coupled to the electronics device 120. For example, the microphone 122 may be incorporated in wired headphones, the microphone 122 may be incorporated in a wireless headset, the microphone 122 may be incorporated in a remote control device, etc.

In some embodiments, the camera module 128 comprises one or more camera devices that include functionality for capturing still and video images, editing functionality, communication interoperability for sending, sharing, etc. photos/videos, etc.

In some embodiments, the electronics device 120 may include any other component suitable for performing a communications operation. For example, the electronics device 120 may include a power supply, ports, or interfaces for coupling to a host device, a secondary input mechanism (e.g., an ON/OFF switch), or any other suitable component.

Figure 3:
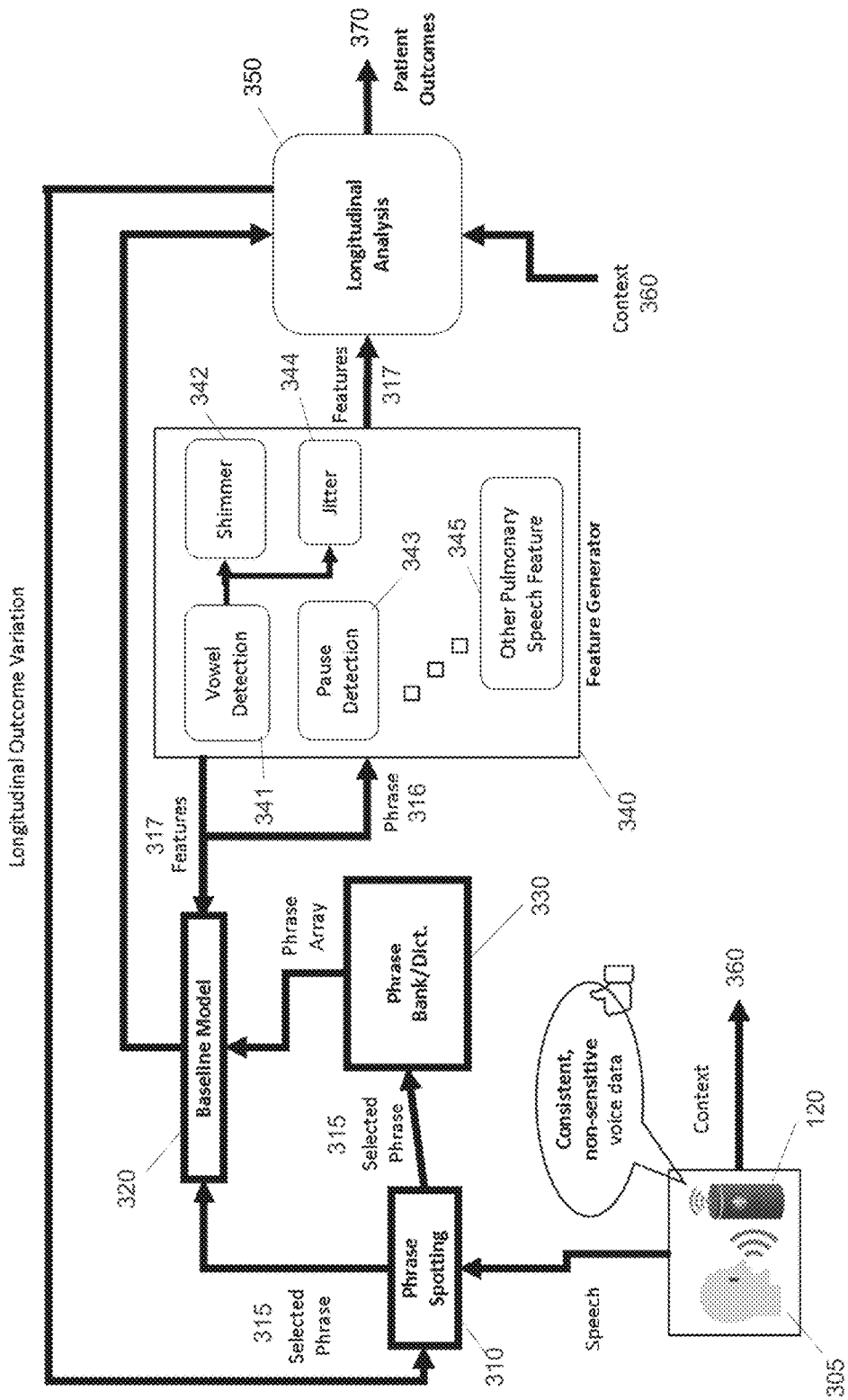
FIG. 3 shows an architecture for voice assistant based health monitoring, according to some embodiments.

FIG. 3 shows an architecture 300 for voice assistant based health (e.g., pulmonary, etc.) monitoring (e.g., the voice assistant health monitoring processing 131, FIG. 2) and analysis, according to some embodiments. The architecture 300 includes phrase spotting processing 310, a baseline (longitudinal) model 320, phrase bank/dictionary (knowledge base) 330, feature generator 340 and longitudinal analysis processing 350. In some embodiments, consistent non-sensitive voice data from a user 305 is received by the voice assistant included in device 120. The voice assistant converts the speech to voice data that is input to the phrase spotting processing 310, and determines context 360 (e.g., device usage, command content, environment, weather, etc.), which is input to the longitudinal analysis processing 350. The phrase spotting processing 310 determines a selected (spotted) phrase 315 that is stored in the phrase bank/dictionary 330. An array of phrases and features 317 (such as speech, sound event, vowel placement, etc.; provided from the feature generator 340) are input to the baseline model 320. The feature generator 340 includes vowel detection processing 341, shimmer processing 342, pause detection processing 343, jitter processing 344 and other pulmonary (or other health issue) speech feature(s) detection processing 345. The baseline model 320 provides phrase data 316 input to the feature generator 340. The features 317 output from the feature generator are input to the longitudinal analysis processing 350. The longitudinal analysis processing outputs a longitudinal outcome variation that is input to the phrase spotting processing 310, and outputs patient outcomes 370. The processing for the architecture 300 is described below in further detail.

Figure 4:
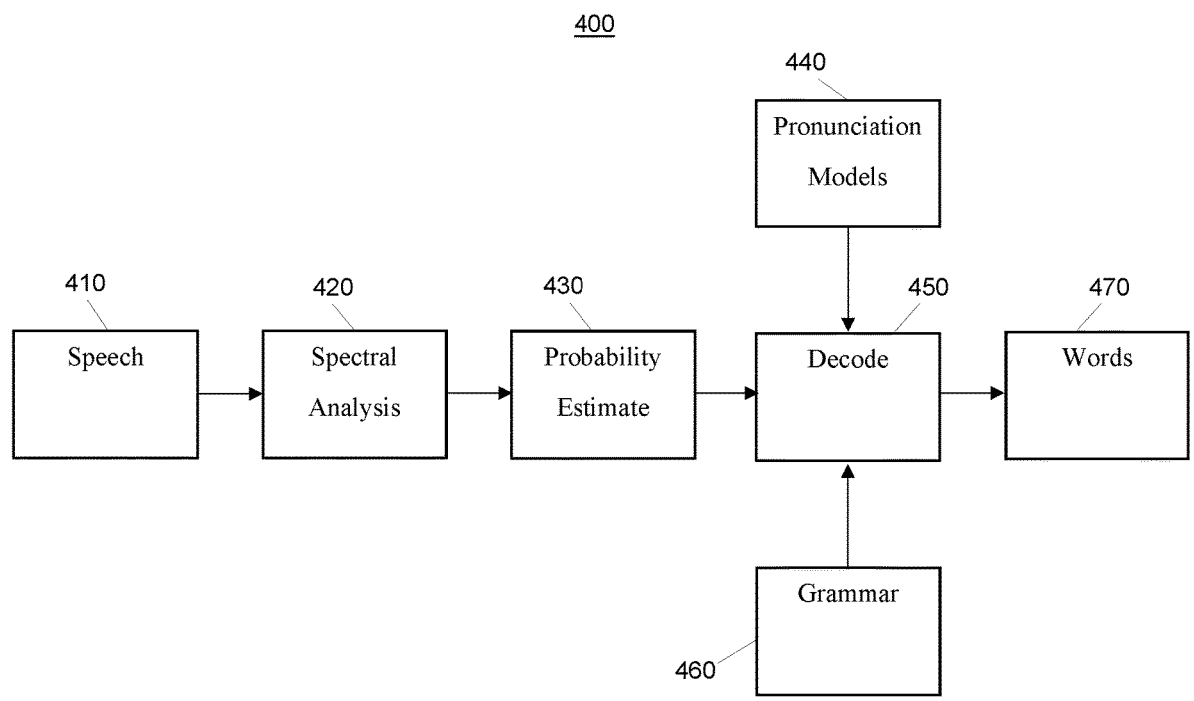
FIG. 4 shows an exemplary speech-to-text process in speech recognition implemented for a voice assistant.

FIG. 4 shows a speech-to-text process 400 in speech recognition implemented for a voice assistant employed by one or more embodiments. Voice assistants are typically triggered by certain commands or sets of commands from the users (e.g., a specific word or phrase, etc.). In the speech-to-text process 400, the speech 410 is analyzed by spectral analysis processing 420 and segmented. Each segment is mapped to a character and eventually a combination of characters forms a word 470. The mapping is performed according to the probability estimate processing 430 of each character given the pronunciation (from the pronunciation models 440), grammar (from grammar processing 460) and semantics (from the decode processing 450). The processing of speech-to-text process 400 is a fundamental step in a voice assistant. Various algorithms or processing using Hidden Markov Models and Deep Neural Networks may be implemented to capture the patterns of speech and conversion to text.

Returning to FIG. 3, as previously discussed above, the commands or set of commands communicated with a voice assistant is limited. Therefore, some embodiments store the common important phrases (combination of words) in the phrase bank/dictionary 330 as a reference for the growing baseline model 320. In other words, some embodiments enable capture of not only the regular patterns, but also the deviation from the pattern baselines for speech and sound events of the patient with respect to each recorded phrase in the phrase bank/dictionary 330.

Figure 5:
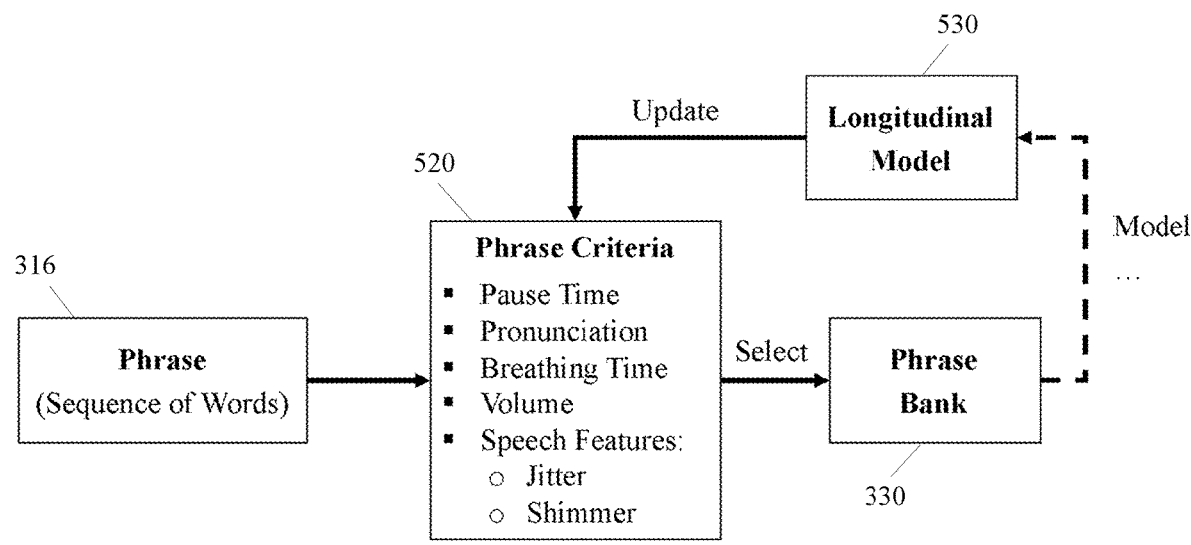
FIG. 5 shows a process flow for phrase spotting criteria for health assessment, according to some embodiments.

FIG. 5 shows a process flow for phrase spotting criteria (for the phrase spotting processing 310, FIG. 3) for health assessment, according to some embodiments. In some embodiments, the focus is for pulmonary patients. Therefore, specific phrase 316 needs to be spotted (by the phrase spotting processing 310, FIG. 3) that are beneficial for feature extraction (by the feature generator 340, FIG. 3) and identifying the user's pulmonary condition. In one or more embodiments, specific initial phrase criteria 520 (such as pause time, pronunciation, breathing time, volume, speech features (jitter and shimmer) is used for selecting the phrases spotted (by the phrase spotting processing 310) using the voice assistant. It should be noted that shimmer refers to the consistency of localized vocal amplitude for voiced sounds, and jitter refers to consistency of localized periodicity of the same. These initial phrase criteria 520 are to be designed in a way that selection of phrases (from the phrase bank/dictionary 330) are most informative for pulmonary assessment. Examples could be phrases with high percentage of vowels or pause time. In some embodiments, the phrase criteria 520 are updated over time as the longitudinal model 530 grows over time.

Figure 6:
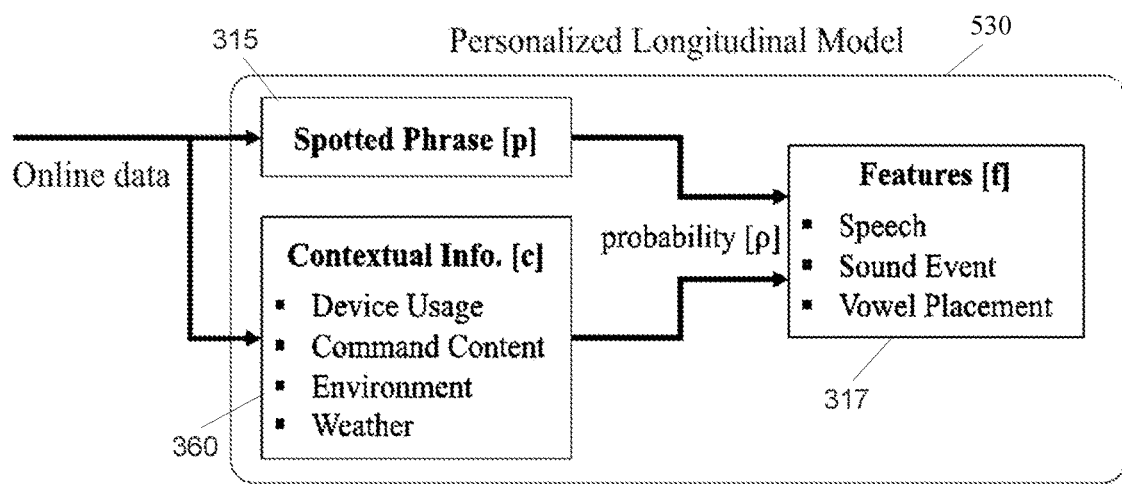
FIG. 6 shows a longitudinal model architecture for capturing personalized correlation and dependencies between spotted phrases, contextual information, and important extracted features from phrases, according to some embodiments.

FIG. 6 shows a longitudinal model 530 architecture for capturing personalized correlation and dependencies between selected (spotted) phrases 315, contextual information 360, and important extracted features 317 from phrases 316 (FIGS. 3 and 5), according to some embodiments. In addition to sound events such as cough, wheezing and throat clearing, analysis of speech for pulmonary applications is effective. One common feature indicative of pulmonary health is pause time pattern and its frequency. Human speech consists of sharp inhalation prior to vocalization, followed by continuous exhalation during vocal production. When respiratory functions are compromised, this can lead to longer inhalation times and/or more frequent pauses for inhalation. Changes in prosodic features of speech such as shimmer and jitter can also be symptomatic of pulmonary illnesses. When vocal cords are affected by pulmonary disease, it can lead to increased shimmer and jitter. Some embodiments implement preliminary processing to generate the baseline for speech feature generation targeted toward pulmonary assessment.

In one or more embodiments, a preliminary energy-threshold-based process is implemented to detect pause time in speech. FIG. 7A shows an example of a waveform 730 for a single subject showing detected speech and pause time segments. The example waveform 730 shows how waveforms may be used for successfully discriminating speech and pause times in a 1-minute sample of speech from a single subject. Some embodiments improve the generalizability and sophistication of the processing to handle background noise in more realistic environmental scenarios. Table I depicts the difference between healthy and pulmonary-related patients based on the measurement from collected data.

TABLE I

| Features | Healthy | | | Patients | | |
| --- | --- | --- | --- | --- | --- | --- |
|  | Min | Max | Mean | Min | Max | Mean |
| Pause Time (ms) | 377.931034 | 719.459459 | 508.687853 | 370 | 898.536585 | 538.527922 |
| Pause Freq (num pauses/min) | 2.80982696 | 14.082173 | 8.96498117 | 2.68428325 | 25.9841175 | 11.6094665 |

Shimmer and jitter features of speech represent the steadiness and consistency of the voice respectively. With pulmonary patients, including Asthma and COPD patients, individuals tend to show relatively higher values of shimmer and jitter. Table II shows measured values for shimmer and jitter for both healthy and pulmonary patient subjects when they performed an "A-vowel" test. A-vowel is a test where participants make a sustained vowel sound ("/a/") for as long as physically possible, with multiple repetitions.

TABLE II

| | Healthy | | | Patients | | |
|---|---|---|---|---|---|---|
| Features | Min | Max | Mean | Min | Max | Mean |
| Shimmer % | 2.64687099 | 9.17153632 | 6.28995262 | 3.89604466 | 28.358845 | 10.3181509 |
| Shimmer Abs (dB) | 0.23058123 | 0.81147117 | 0.5590437 | 0.34189185 | 2.6465896 | 0.94222707 |
| Jitter % | 0.40721244 | 2.67019273 | 1.34884145 | 0.63756509 | 14.6169476 | 5.94135035 |
| Jitter Abs (µs) | 39.5435929 | 220.699849 | 117.559113 | 49.989768 | 1807.85996 | 476.26984 |

Although distinguishing healthy and non-healthy individuals might seem feasible using a vowel test such as the "A-vowel" test, the problem is not at all trivial when a stream of speech is used as the input of analysis instead of a single sustained vowel. In a stream of speech where vowel and consonant parts are not clearly distinguished, shimmer and jitter estimates can be drastically misleading. It is thus necessary to discover the vowel parts of the speech first and then measure the shimmer/jitter on those parts only. This solution, however, is not trivial and segmentation of voiced sounds (i.e. vowels) is difficult for natural speech.

Figure 7B:
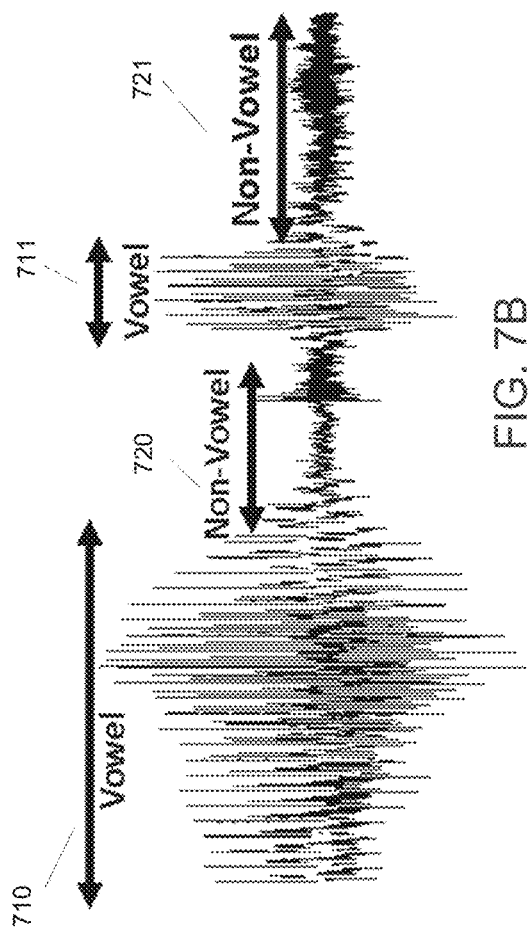
FIG. 7B shows an example of a wave form showing vowel and non-vowel portions for the speech signal.
Figure 7A:
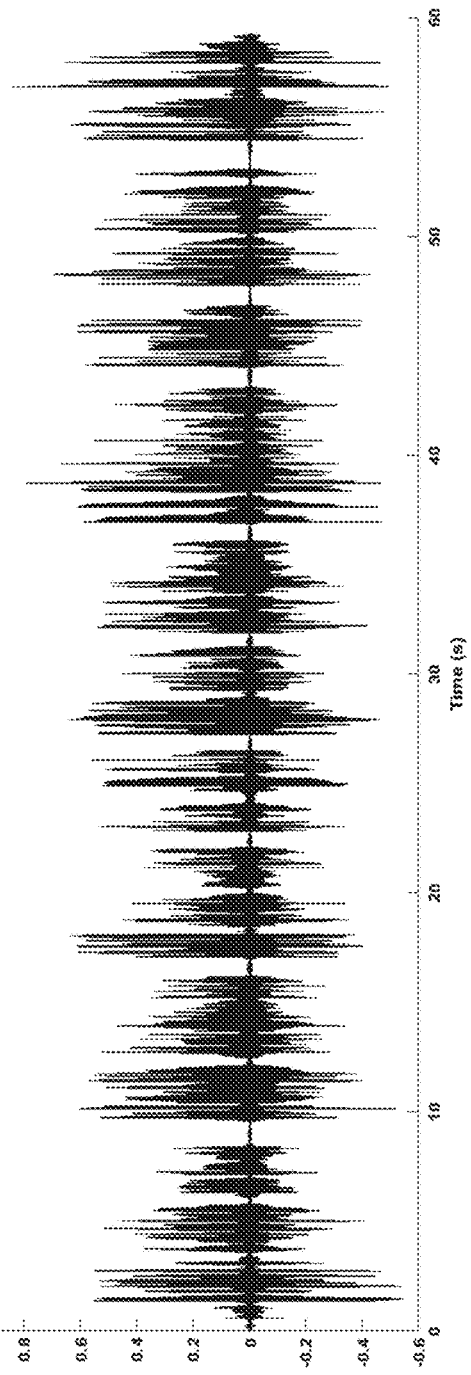
FIG. 7A shows an example of a waveform for a single subject showing detected speech and pause time segments.

FIG. 7B shows an example of a wave form showing vowel 710/711 and non-vowel 720/721 portions for the speech signal. Some embodiments implement a machine-learning based processing for classifying vowels and non-vowels using a known dataset referred to as TIMIT (a corpus of phonemically and lexically transcribed speech of American English speakers of different sexes and dialects). Using 20 Mel Frequency Cepstral Coefficient (MFCC) features, some embodiments achieve an accuracy of about 85% in classification of vowels. These results are for data that is collected in a controlled setting where the effect of the noise is minimal. However, for natural speech data collection there is no control over the type, extent and intensity of the noise coming from the surroundings of the user. Therefore, in some embodiments these issues are solved using voice assistant data as the input.

Returning to FIG. 6, in some embodiments, for the baseline model 320 (FIG. 3), online learning is used to generate the baseline model 320 personalized for the participant (pulmonary patient). The baseline model 320 captures the longitudinal series of data captured by the voice assistant. The data contains the contextual information 360 alongside the features 317 extracted from the speech and the sound events after spotting the common phrases (spotted phrase 315). The online learning optimizes the baseline model 320 parameters given the training data, which is the spotted phrases 315 by the voice assistant. The features 317 are extracted from the spotted phrase 315 given the condition of the contextual information 360. The baseline model 320 captures the correlation and dependencies between the extracted features 317 and the spotted phrase 315 in the given condition. Since the spotted phrases 315 are generated as the result of interaction between the patient and the voice assistant, the longitudinal model 530 becomes personalized. In one or more embodiments, the baseline model 320 is trained using a participatory scheme. In this participatory scheme, instead of, or in addition to, waiting for the patient to express certain phrases and using the spotted phrase(s) 315 for training the baseline model 320, the data collection devices (e.g., a smartwatch and smartphone) or even the voice assistant itself proactively asks the patient to provide sentences of interest. The provided sentences obtained with the proactive participatory scheme are then provided as training data for the baseline model 320 to improve accuracy.

Figure 8:
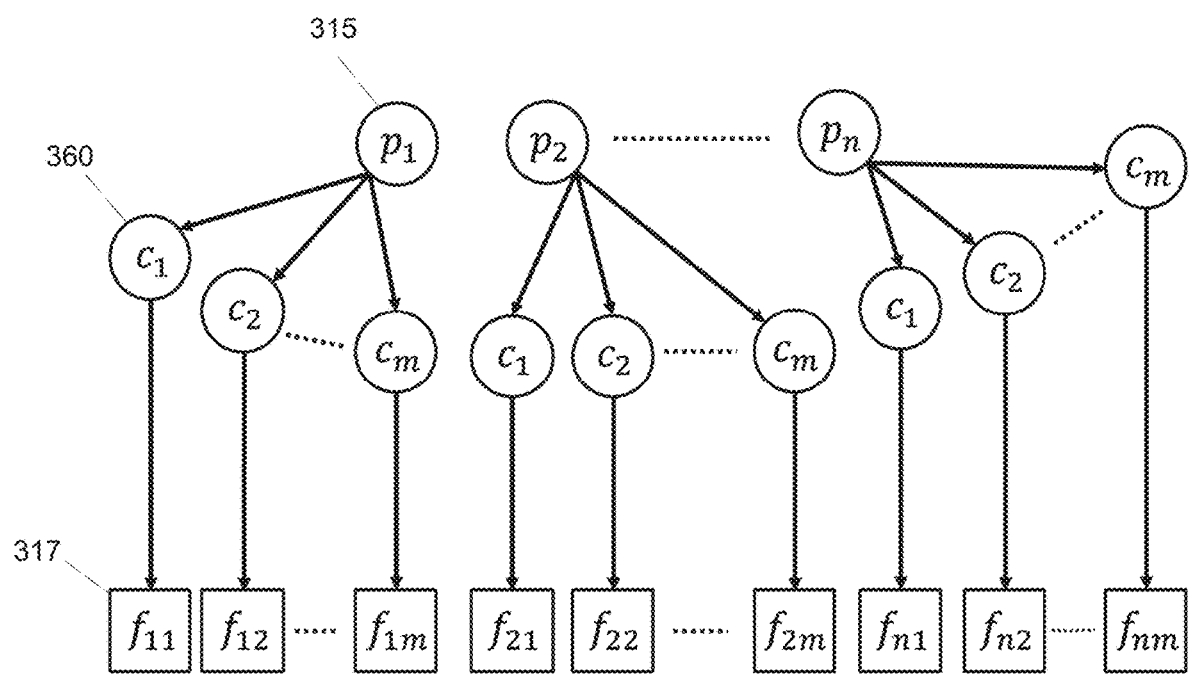
FIG. 8 shows an example for features generated under different contexts for the spotted phrases (state model) forming the personalized longitudinal model, according to some embodiments.

FIG. 8 shows an example for features 317 generated under different contexts for the spotted phrases 315 (state model) forming the personalized longitudinal model 530 (FIGS. 5 and 6), according to some embodiments. In one or more embodiments the pulmonary-related features 317 capture the state of the pulmonary patient in various contexts, which will be useful in assessing the patient health related to their vocal cords, lung, and other aspects.

Figure 9:
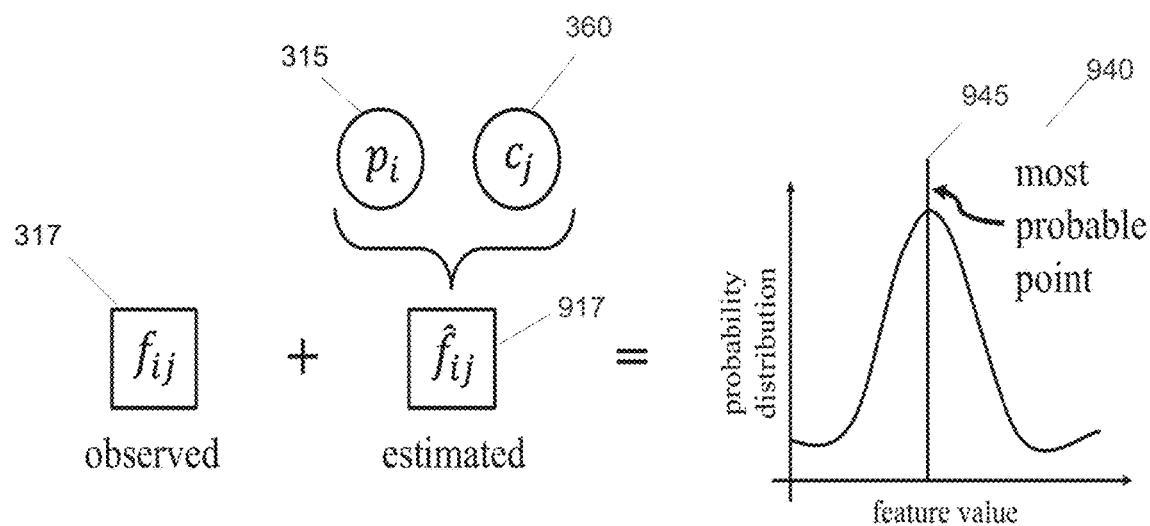
FIG. 9 shows an example for improving the model estimation and feature evaluation accuracy by feeding the estimated data back to input, according to some embodiments.

FIG. 9 shows an example for improving the personalized longitudinal model 530 (FIGS. 5 and 6) estimation and feature evaluation accuracy by feeding the estimated feature 917 data back to input, according to some embodiments. In some embodiments, various processing algorithms are available that enable the online learning capability. Hidden Markov Modeling, Reinforcement Learning, and Kalman Filters may be employed for various longitudinal data to capture the statistical information of gradual changing behavior in humans, vehicles, etc. The generated personalized longitudinal model 530 is further trained at runtime by feeding more up-to-date data. The statistical parameters and dependencies between existing phrases and contextual information are adjusted. New spotted phrases 315 and conditions are gradually inserted into the personalized longitudinal model 530 to capture wider scenarios.

In some embodiments, evaluation of features 317 for speech and sound events is not a deterministic process and involves variations and dependencies unforeseen in any model. The personalized longitudinal model 530 updating process uses the current statistical information captured in the personalized longitudinal model 530 to more accurately evaluate the features 317 for future spotted phrases 315. Conventional speech recognition techniques can adapt to the personalized pronunciation of the user for more accuracy in speech recognition. In one or more embodiments, the personalized longitudinal model 530 will not only help in more accurate speech recognition, but also in more accurate symptom identification and speech feature 317 extraction. For instance, probability distribution 940 of the vowel placement in a spotted phrase 315 can help the speech recognition system to more accurately identify the phrase and also locate the vowels more accurately (e.g., most probable point 945) for speech feature evaluations such as pause time, shimmer, jitter, etc.

Some embodiments involve an auto-regressive model that utilizes the estimated output of past phrases as inputs for future training and prediction. This mechanism of feedback of the past estimation to future input helps the personalized longitudinal model 530 adapt to the intrinsic error of speech recognition and feature extraction over time without the need for any significant extra computation power. In one or more embodiments, the personalized longitudinal model 530 is further personalized and the outputs will be more accurate. In some embodiments, this mechanism may be utilized in time series data prediction as part of Recurrent Neural Networks, Nonlinear AutoRegressive with Exogenous Inputs (NARX), etc.

In some embodiments, the generated baseline model 320 (FIG. 3) is used as the baseline for predicting the state of the subject during the interaction with the voice assistant given an unseen condition (contextual information 360). The prediction assists in foreseeing any significant deviation from the already-captured features in the baseline model 320. For instance, drastic deviation of the speech features 317 extracted from the spotted phrase 315 in a specific context from the baseline model 320 (trained model), may be a sign of exacerbation in an asthma patient. This situation can be predicted or even prevented. The threshold of the deviation from the baseline is very dependent on each person and their tolerance to various conditions. The statistical information captured in the baseline model 320 enables evaluation of the tolerance of a person to various conditions and act accordingly.

In one or more embodiments, besides speech-based pulmonary assessment, assessment based on detection of relevant lung sounds may also be implemented. In some embodiments, detection of lung sounds such as cough, wheeze, etc., using devices 120 (FIG. 2) is implemented including processing cough classification. Any sound events captured in the recorded audio during the interaction with the voice assistant provides useful features that enable identification of pulmonary patient health condition.

Figure 10:
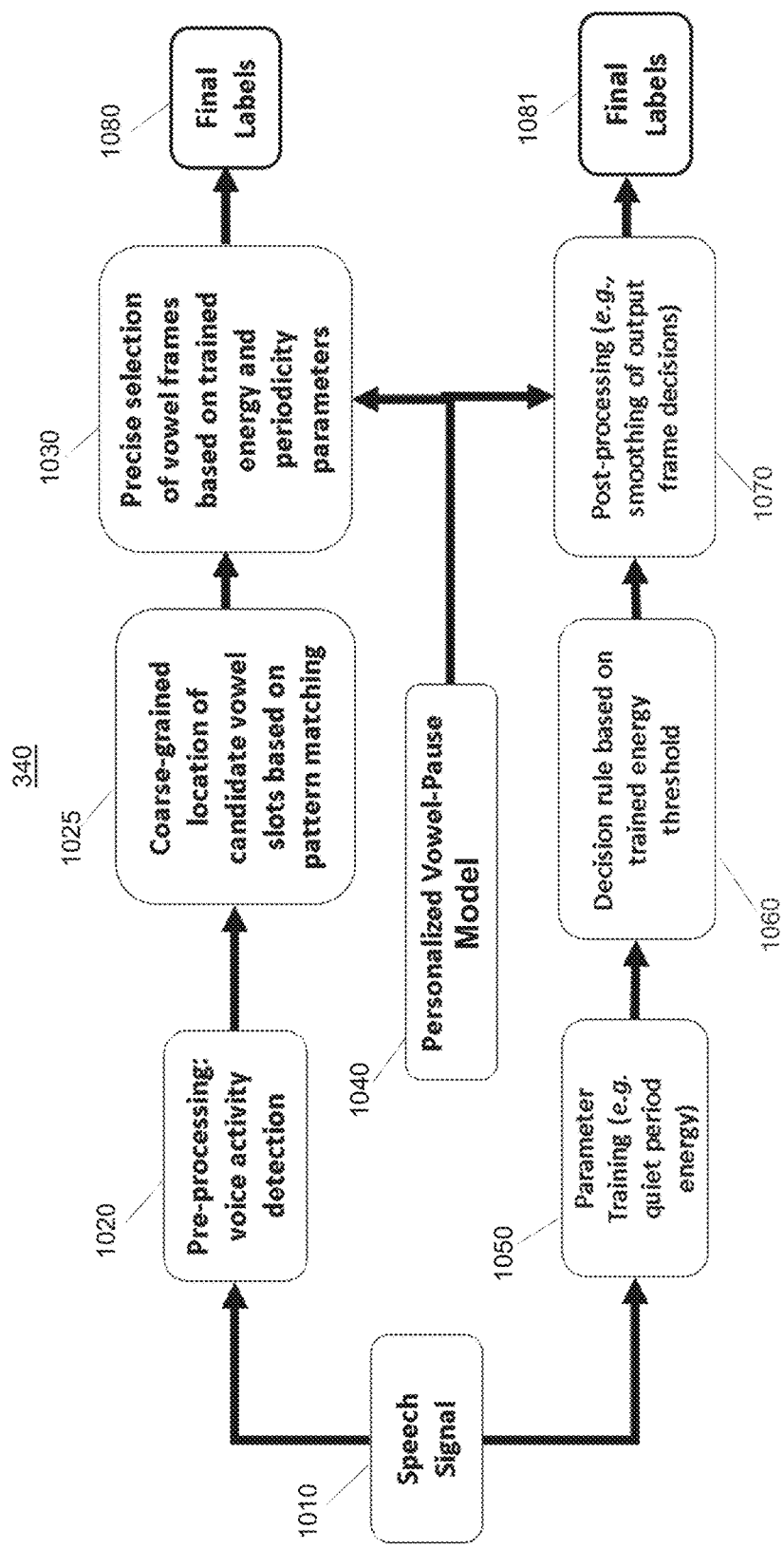
FIG. 10 shows a block diagram for feature generation, according to some embodiments.

FIG. 10 shows a block diagram for feature generator 340, according to some embodiments. In one embodiment, the speech signal from block 1010 is input to pre-processing block 1020 including voice activity detection. From the pre-processing block 1020, block 1025 processing includes coarse-grained location of candidate vowel slots based on pattern matching (see, e.g., FIG. 7B). Block 1030 processing includes precise selection of vowel frames based on trained energy and periodicity parameters, which uses input from block 1040 processing including a personalized vowel-pause model. From block 1030, final (classification) labels 1080 (i.e., vowel labels: vowel or non-vowel) are output. Additionally, block 1050 receives the speech signal from block 1010 and performs processing including parameter training (e.g., quiet period energy). In block 1060, processing includes a decision rule based on a trained energy threshold. Block 1070 includes the output from blocks 1060 and 1040, and includes post-processing (e.g., smoothing of output frame decisions). From block 1070, final (classification) labels 1081 (i.e., pause labels: pause or non-pause) are output.

Figure 11:
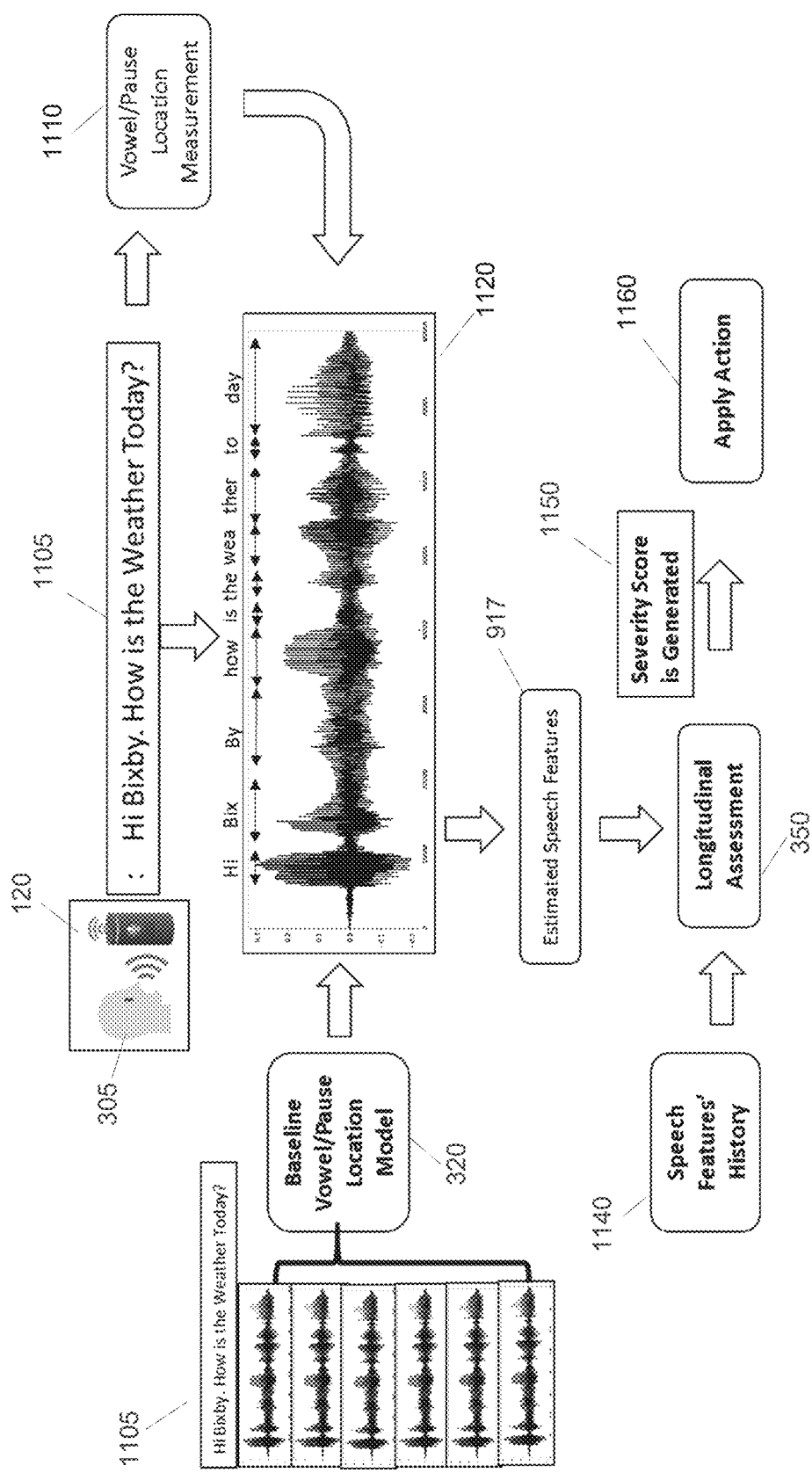
FIG. 11 shows an example use case for analyzing a phrase and determining a severity score and applying actions for health monitoring, according to some embodiments.

FIG. 11 shows an example use case for analyzing a phrase 1105 and determining a severity score and applying actions for health monitoring, according to some embodiments. In some embodiments, the example begins with the user 305 providing the speech 1105 "Hi Bixby. How is the weather today?" that is received by the voice assistant on an electronic device 120 (FIG. 2). The voice assistant health monitoring processing 131 (FIG. 2) inputs the speech signal from the received speech 1105 into the baseline vowel/pause model 320 and also into the vowel/pause location measurement processing 1110. The output from the baseline vowel/pause model 320 and the vowel/pause location measurement processing 1110 for the waveform 1120 results in the estimated speech features 917 that are input to the longitudinal assessment processing 350, which also takes as input speech features' history data 1140. The result generated from the longitudinal assessment processing 350 is a severity score 1150. The severity score 1150 is to cause an application of an action as follows. In some embodiments, if the severity change (from a baseline score) is more than a predefined threshold, one or more of the following actions may occur: the patient is notified (e.g., on the electronic device 120); more measurement is initiated by on-spot engaging of the patient; and if needed, clinicians are informed. If the severity change is less than the predefined threshold, one or more of the following actions may occur: recording of speech features; and updating the models. If the longitudinal assessment 350 indicates emergence of an exacerbation event, one or more of the following actions may occur: notify the patient to use an inhaler; notify clinicians for a quick intervention; and call 911 if needed.

Figure 12B:
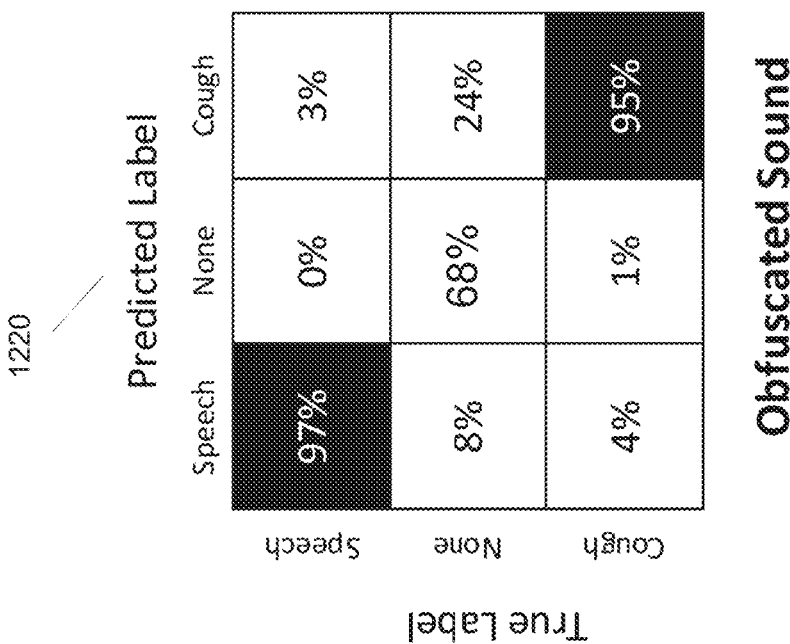
FIG. 12B shows an example confusion matrix for cough/speech/none classification using random forest for obfuscated audio data, according to some embodiments.
Figure 12A:
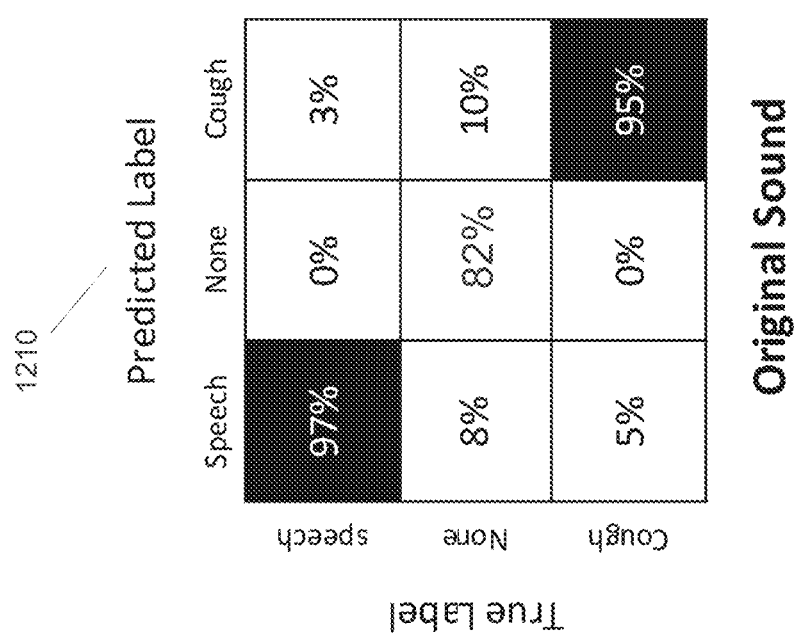
FIG. 12A shows an example confusion matrix for cough/speech/none classification using random forest for non-obfuscated audio data, according to some embodiments.

FIG. 12A shows an example confusion matrix 1210 for cough/speech/none classification using random forest for original sound (non-obfuscated audio data), according to some embodiments. FIG. 12B shows an example confusion matrix 1220 for cough/speech/none classification using random forest for obfuscated sound (audio data), according to some embodiments. In one embodiment, recorded data is filtered using processing for preserving privacy and then uploaded to a remote server (e.g., cloud/server 140, FIG. 2) for storage and analysis. The filtering processing operates on 30 ms audio frames with a 10 ms step size. For each audio frame Linear Predictive Coding (LPC) coefficients, gain and whether or not the frame was voiced are calculated. For frames that are voiced, the LPC coefficients are replaced with a randomly chosen set of coefficients for pre-recorded vowel sounds. Therefore, the speech is obfuscated and becomes unintelligible.

In some embodiments, the obfuscation processing does not significantly affect classification performance, and represents a feasible block of the framework for privacy preserving cough detection. In terms of intra-class deterioration, it should be noted that "Speech" and "Cough" are not as affected as "None" class (only about 8%). This is encouraging due to the fact that eventually a lot of "None" class segments will be filtered out by the "sound event detector" anyway, before getting to the obfuscation and classification processing.

Figures 13A, 13B:
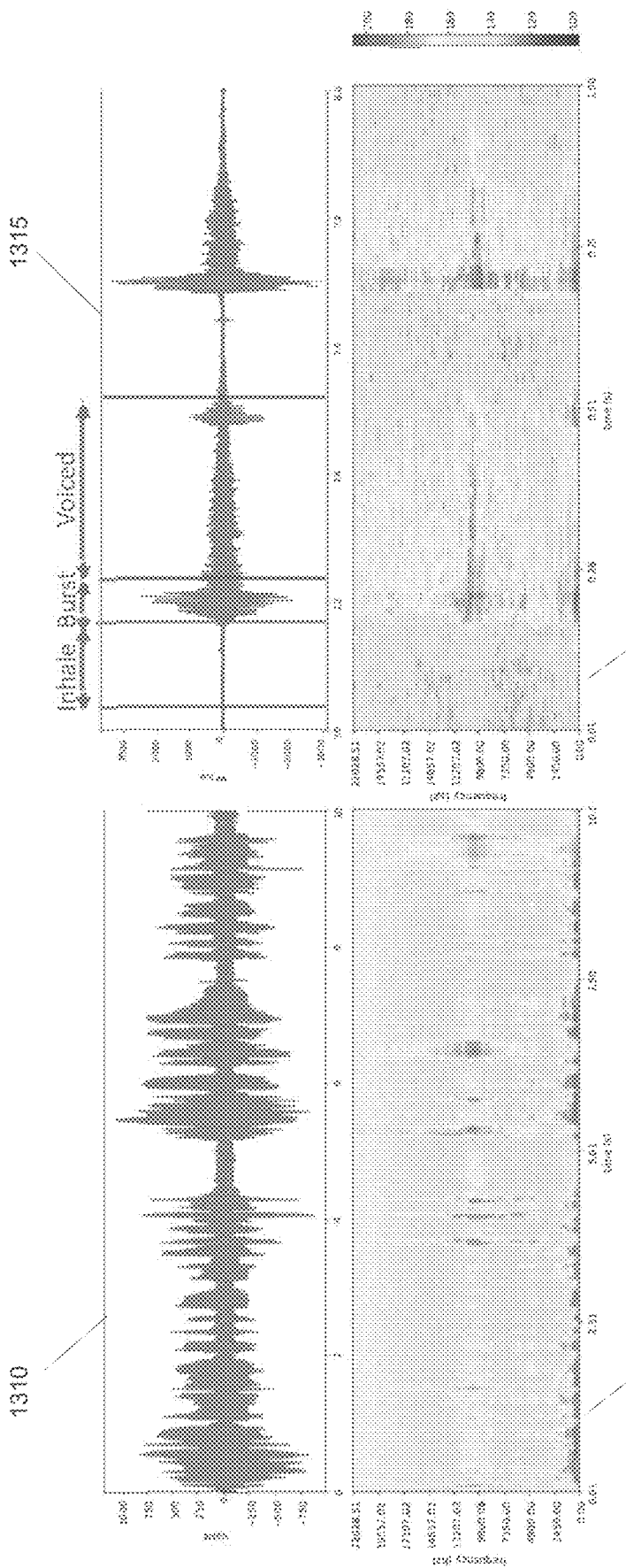
FIG. 13A shows an example speech waveform (top) and spectrogram (bottom)
FIG. 13B shows an example cough waveform (top) and spectrogram (bottom)
Figure 14:
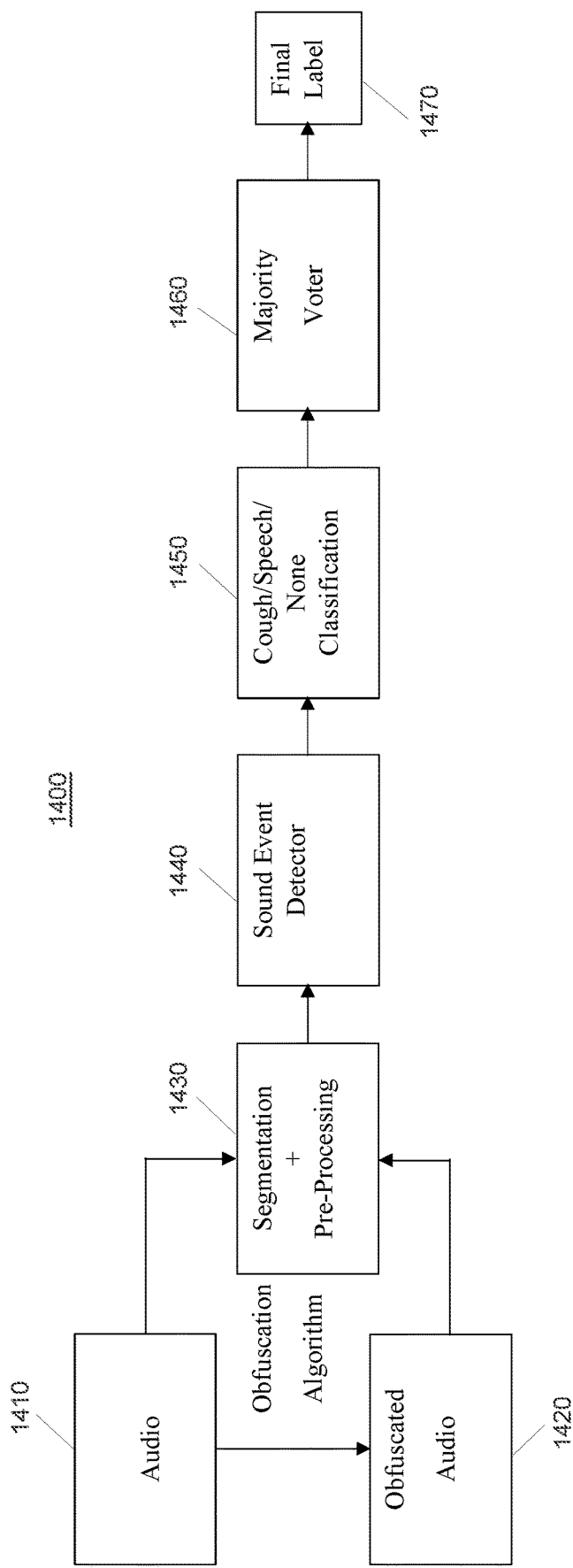
FIG. 14 shows a block diagram for architecture of cough detection processing, according to some embodiments.

FIG. 13A shows an example speech waveform 1310 (top) and spectrogram 1320 (bottom). FIG. 13B shows an example cough waveform 1315 (top) and spectrogram 1325 (bottom). A spectrogram is the visual representation of the spectrum of frequencies of a sound as they vary with time. It can be seen that these audio events carry specific characteristics, which enable the two to be distinguished. The sensing architecture 1400 can be seen in FIG. 14. In some embodiments, a "sound event detector" 1440 (FIG. 14) filters out the non-interesting parts of the audio. Then cough vs. speech vs. none classification is performed by the cough/speech/none classification processing 1450 (FIG. 14). Eventually, a majority voter processing 1460 (FIG. 14) smooths the output labels of the classifier. Using this structure classification between cough, speech and other sound events are performed with a relatively high accuracy.

In order to be able to detect cough patterns and model them, some embodiments first observe the cough waveform and visualize its frequency components. A spectrogram (e.g., example spectrogram 1325) is used to observe a cough manifestation from an audio stream. The speech waveform 1310 has a 10-second duration and the cough sample waveform 1315 includes two cough events and is chosen to have a 1-second duration for better visualization of cough phases. Although there can be variations across different individuals and disease states, the cough reflex consists of four main phases in general as follows: an initial large inhalation and glottis closure; diaphragm and external intercostal muscles contract against the closed glottis; the vocal cords reflex and an explosive burst of air exits the lungs; and a voiced sound as the exhalation continues.

The waveform 1315 clearly shows that the burst and the voiced part of the cough can be identified in the audio signal, and therefore can be automatically detected by one or more embodiments. The accumulated duration of these two parts is different across individuals and varies between 300 to 500 ms. In addition to the duration, coughs have other unique characteristics, such as loud intensity and a specific frequency range. This can be observed in the spectrogram 1325 of the cough as well. It is evident that the loudness and the frequency components of the cough are very different than those of normal speech. In order to be able to detect these unique features, a hierarchical structure is implemented in architecture 1400 (FIG. 14).

FIG. 14 shows a block diagram for architecture 1400 of cough detection processing, according to some embodiments. Both raw audio 1410 and the obfuscated version of the audio (obfuscated audio 1420) can be fed to the architecture 1400 for cough detection. After segmentation and pre-processing 1430 of the input audio, segments with significant audio events are found using the sound event detector 1440 (first stage). Then classification of "Cough" vs. "Speech" vs. "None" (second stage) is performed by the cough/speech/none classification processing 1450, and eventually the majority voter processing 1460 (third stage) using a majority voting algorithm chooses the final label 1470 based on the results of the classification of each frame in the processed time window. One benefit of the three-stage structure of architecture 1400 is that a large portion of the audio will be discarded after passing the first stage. This leaves only a small portion to be further processed in the second and third stages (which consume more processing power and energy). Overall, this helps the whole cough detection processing be less power-hungry and time consuming, making it suitable for implementing on mobile devices.

A large portion of the collected audio on a daily-basis can carry information that is not of interest. This can include environmental outdoor noise, TV sounds, and the sounds of people having conversations around the device (e.g., an electronic device 120). In some embodiments, the objective of the sound event detector 1440 is to filter out these parts of the audio to be able to reduce the burden on the following stages. On the other hand, no sound events of interest should be rejected in the process. Coughs, speech and similar events of interest usually carry higher energy and sudden change of amplitude. Whereas, for instance, a fan running in the background carries lower energy and a flatter signal amplitude. While some of the conventional algorithms use only energy or standard deviation (STD) within a time frame to filter out these parts, it is important to realize that the energy of the frame by itself is not sufficient to detect a sound event. A fan can be running very close to the recording device, making the amplitude of the signal and its energy high, although this should not be considered an event. The same energy threshold cannot be used to filter out the non-interesting parts of the audio file. Instead, in some embodiments the relative energy and STD (Eq. 1) is used by the sound event detector 1440.

$$\text{Relative Energy:} \frac{\sum_{0}^{N} a_i^2}{\sum_{0}^{M} a_j^2} \quad \text{(Eq. 1)}$$

$$\text{Relative STD:} \sqrt{\frac{\sum_{0}^{N}(a_i - \bar{a})}{N}} \Big/ \sqrt{\frac{\sum_{0}^{M}(a_j - \bar{a})}{M}}$$

where $a_i$ represents a sample in the wave vector and $\bar{a}$ is the mean of the vector for the selected time window. N and M are two parameters incorporated to fulfil this relative notion (N being the number samples in a time window and M being the number of samples in the surrounding of the time window with size of multiple time windows). In some embodiments, N is selected to be the number of samples in 1 second, which represents the maximum duration of a sound event. In some embodiments, M is selected to be 10 seconds; wide enough to represent the general energy level and STD of the environment that the user is in, while not so wide as to be irrelevant to the corresponding sound event. If a time window is tagged with an event, one window (500 ms) before and one window after that are also considered to be events to make sure not to miss any important piece of information. Using this processing, the quiet part of the audio will be removed in the first stage, along with the parts with low-enough energy (environmental noise) to be considered "non-events."

In some embodiments, once events are recognized by the sound event detector 1440, they need to be analyzed as potential cough events. Supervised machine learning may be implemented for this in some embodiments. As the target for the processing of architecture 1400 is mainly indoor cough detection, it is assumed that the main sources of sound, other than the environmental non-interesting part, is cough (or similar to cough symptoms such as sneeze) and speech. Therefore, a classification task between cough, speech and none (neither of the two) classes (via the cough/speech/none classification processing 1450).

In some embodiments, for segmentation and pre-Processing 1430 and feature extraction, the cough, speech and none wave sources are de-noised using a high-pass filter with corner frequency of 200 Hz (to address frequency range of cough and speech). Then the data is segmented using a sliding window algorithm with 500 ms window size (the maximum duration of a cough event) and 50 ms jump size and Hamming window function. In one example, a total of 61 features including 42 MFCC features, total energy, zero crossing and some other spectral features such as spectral variance, kurtosis and skewness are generated. These features are then normalized and fed to machine learning algorithms.

In some embodiments, for the cough/speech/none classification processing 1450, a random forest classifier may be implemented. In other embodiments, other classifiers may be implemented, such as Logistic Regression, SVM, MultiLayer Perceptron (MLP), etc. In the first stage (sound event detector 1440), the possibility of each one-second window to contain sound events is assessed. The one-second windows with sound events are fed to the cough/speech/none classification processing 1450 in the second stage. After segmentation in the second stage, each one-second window contains ten 500-ms frames. Each of the frames are labeled using the classification in the second stage. The purpose of the third stage (majority voter processing 1460) is to determine if the one-second window is cough, speech or none, based on the individual classes of the constituent phrase. This third stage applies a smoothing function on the often-discrepant outcome sequence of the classifier. As an example, the classification results (which has resolution of 50 ms) might have six cough labels in one-second window time. This does not mean there has been six coughs in that 1 second.

Figure 15:
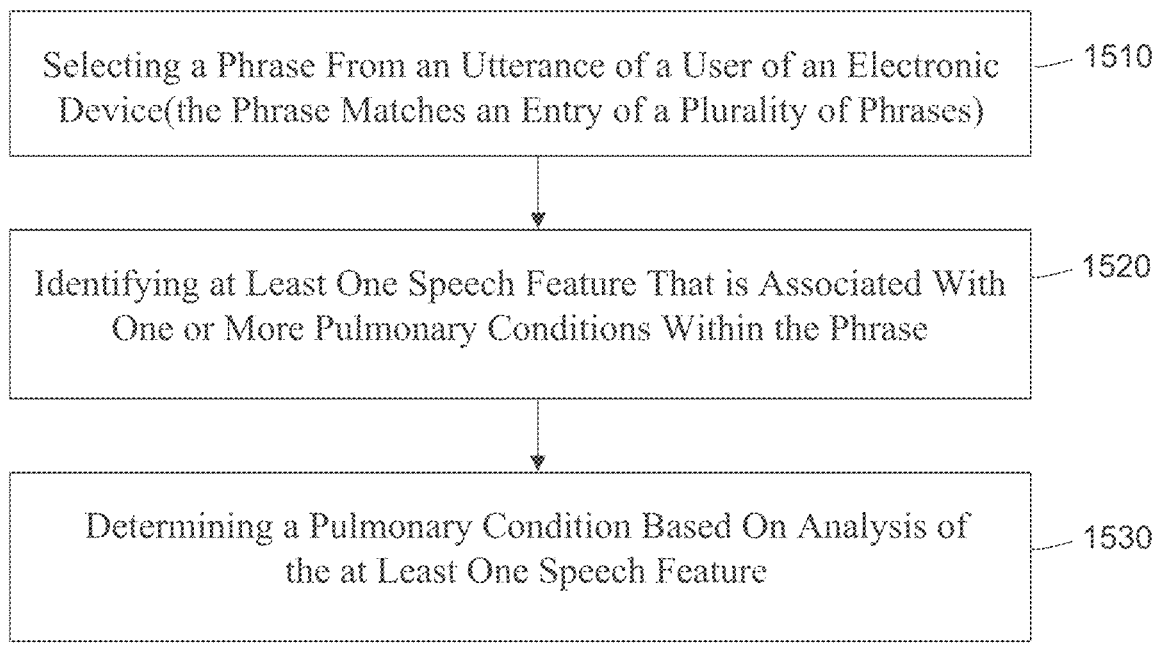
FIG. 15 shows a block diagram of a process for detection, analysis and action for pulmonary patients using voice assistant, according to some embodiments.

FIG. 15 shows a block diagram of a process 1500 for detection, analysis and action for pulmonary patients using voice assistant, according to some embodiments. In some embodiments, block 1510 of process 1500 provides for selecting a phrase from an utterance (e.g., using phrase spotting processing 310, FIG. 3) of a user of an electronic device (e.g., electronic device 120, FIG. 2, system 1600, FIG. 16, etc.). The phrase matches an entry of multiple phrases (e.g., in the phrase bank/dictionary 330, FIG. 3). Block 1520 of process 1500 provides for identifying at least one speech feature (e.g., from feature generator 340, FIGS. 3 and 10) that is associated with one or more pulmonary conditions within the phrase. Block 1530 of process 1500 provides for determining a pulmonary condition based on analysis (e.g., longitudinal analysis 350, FIG. 3) of the at least one speech feature.

In some embodiments, in process 1500 the at least one speech feature includes one of: pause within the phrase, vowel within the phrase, or a combination thereof. The analysis of the at least one speech feature includes comparing the speech feature with a knowledge base (e.g., phrase bank/dictionary 330, FIG. 3). In some embodiments, process 1500 may include determining, triggering, and/or applying an action (e.g., apply action processing 1160, FIG. 11) based on the determined pulmonary condition.

In one or more embodiments, process 1500 may include updating the knowledge base as a result of the analysis of the at least one speech feature. Process 1500 may additionally include retrieving an expected position of the at least one speech segment based on the knowledge base, determining position of the at least one speech segment based on the expected position and generating the at least one speech feature for the at least one speech segment.

In some embodiments, process 1500 may further include identifying at least one pause within the phrase, and determining the pulmonary condition based on analysis of pause duration and pause pattern of the at least one pause. Process 1500 may additionally include receiving a context (e.g., context 360, FIGS. 3 and 6, accompanying the utterance, and determining the pulmonary condition based on analysis of the at least one speech feature in view of the context (e.g., via longitudinal analysis processing 350, FIGS. 3 and 11).

In one or more embodiments, in process 1500 the utterance is obtained passively or proactively from the user of the electronic device. A baseline model (e.g., baseline model 320, FIGS. 3 and 11) captures correlation and dependencies between the one or more speech features and the selected phrase for a condition. The baseline model is personalized (e.g., personalized longitudinal model 530, FIG. 6) as a result of interaction between the user of the electronic device and a voice assistant connected to the electronic device.

In some embodiments, process 1500 may include detecting a cough from the utterance, analyzing features of the cough (see, e.g., architecture 1400). In one or more embodiments, determining the pulmonary condition is further based on the analysis of the features of the cough.

In some embodiments, besides the voice data, other sources may be used for pulmonary assessment (and in a broader scope, general well-being assessment). Device usage information from the voice assistant, such as usage frequency, usage pattern, and usage timing can be beneficial for contextual information. For example, changes in the frequency of using the voice assistant by the patient, may indicate worsening of the symptoms of the patient. In some embodiments, content of the command that the patient is performing may be used as an indicator of his/her pulmonary disease state. For instance, searching for a specific drug or about specific symptoms with regards to a specific disease. This information can be easily extracted using the voice assistant API and speech-to-text processing.

In one or more embodiments, location where the phrase is spotted or command was triggered is a contextual information that will enable processing to have the prior knowledge of the environment the patient is located. For instance, the air quality, noise level, population in the area, room size, etc. are major features of an environment which can influence the pulmonary patient condition. Room temperature, pressure, and ambient lighting are other sensory data that define the current condition of the environment where the patient is located. Opportunistically physiological data from other devices such as heart rate from a smartwatch can be incorporated to understand the current context of the patients, especially when the user reduces using the interactions with the system due to worsening condition. The contextual information will provide more features that will influence the patient speech pattern and symptoms with regards to their pulmonary condition. Analysis of the audio data without context, limits the ability to have an accurate longitudinal analysis model for each patient. Furthermore, the model provides for predicting the condition of the participant in an unseen environment in order to intervene and warn the participant before any serious and dangerous condition arises.

In one or more embodiments, the audio is collected in a passive manner upon the participant usage of voice assistant. This way the data collection scheme is opportunistic rather than participatory. This automatically removes all the complications regarding participant adherence. In addition, as a result of passive sensing, the collected speech is not artificial (obtained in a natural way). In some embodiments, the architecture 300 (FIG. 3) and 1400 (FIG. 14) are implemented in a participatory scheme. In this participatory scheme, instead of waiting for the patient to express certain phrases, the data collection devices (e.g., a smartwatch and smartphone) or even the voice assistant itself proactively asks the patient to denote those sentences of interest. In this way, the number of interesting data points will increase linearly dependent to the extent of demand. However, it will increase the patient burden and it may raise many privacy-related concerns. In some embodiments, the proactive processing can occasionally pop-up certain notifications in different times and locations (based on the level of interest of patient in participation) and ask the patient to express sentences that the proposed passive sensing processing found interesting.

Figure 16:
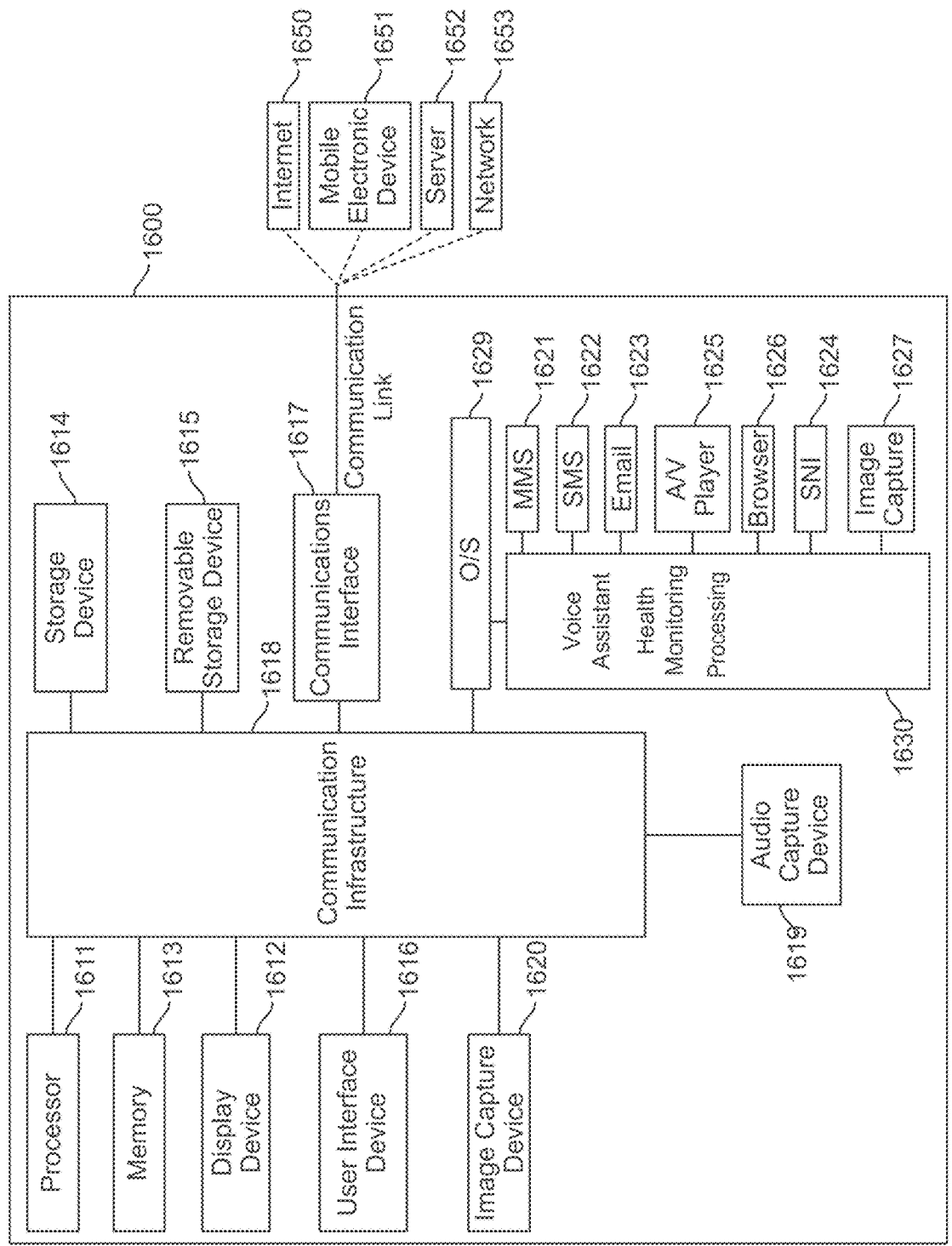
FIG. 16 is a high-level block diagram showing an information processing system comprising a computing system implementing one or more embodiments.

FIG. 16 is an exemplary high-level block diagram showing an information processing system comprising a computing system implementing one or more embodiments. The system 1600 includes one or more processors 1611 (e.g., ASIC, CPU, etc.), and may further include an electronic display device 1612 (for displaying graphics, text, and other data), a main memory 1613 (e.g., random access memory (RAM), cache devices, etc.), storage device 1614 (e.g., hard disk drive), removable storage device 1615 (e.g., removable storage drive, removable memory, a magnetic tape drive, optical disk drive, computer-readable medium having stored therein computer software and/or data), user interface device 1616 (e.g., keyboard, touch screen, keypad, pointing device), and a communication interface 1617 (e.g., modem, wireless transceiver (such as Wi-Fi, Cellular), a network interface (such as an Ethernet card), a communications port, or a PCMCIA slot and card).

The communication interface 1617 allows software and data to be transferred between the computer system and external devices through the Internet 1650, mobile electronic device 1651, a server 1652, a network 1653, etc. The system 1600 further includes a communications infrastructure 1618 (e.g., a communications bus, cross bar, or network) to which the aforementioned devices 1611 through 1617 are connected.

The information transferred via communications interface 1617 may be in the form of signals such as electronic, electromagnetic, optical, or other signals capable of being received by communications interface 1617, via a communication link that carries signals and may be implemented using wire or cable, fiber optics, a phone line, a cellular phone link, a radio frequency (RF) link, and/or other communication channels.

In one implementation of one or more embodiments in an electronic device (e.g., electronic device 120, FIG. 2), the system 1600 further includes an image capture device 1620, such as a camera 128 (FIG. 2), and an audio capture device 1619, such as a microphone 122 (FIG. 2). The system 1600 may further include application processing or processors as MMS 1621, SMS 1622, email 1623, social network interface (SNI) 1624, audio/video (AV) player 1625, web browser 1626, image capture 1627, etc.

In one embodiment, the system 1600 includes voice assistant health monitoring processing 1630 that may implement processing similar as described regarding architecture 300 (FIG. 3), architecture 1400 (FIG. 14), and process 1500 (FIG. 15), as described above. In one embodiment, the voice assistant health monitoring processing 1630 along with an operating system 1629 may be implemented as executable code residing in a memory of the system 1600. In another embodiment, the voice assistant health monitoring processing 1630 may be provided in hardware, firmware, etc.

In one embodiment, the main memory 1613, storage device 1614 and removable storage device 1615, each by themselves or in any combination, may store instructions for the embodiments described above that may be executed by the one or more processors 1611.

As is known to those skilled in the art, the aforementioned example architectures described above, according to said architectures, can be implemented in many ways, such as program instructions for execution by a processor, as software modules, microcode, as computer program product on computer readable media, as analog/logic circuits, as application specific integrated circuits, as firmware, as consumer electronic devices, AV devices, wireless/wired transmitters, wireless/wired receivers, networks, multi-media devices, etc. Further, embodiments of said Architecture can take the form of an entirely hardware embodiment, an entirely software embodiment or an embodiment containing both hardware and software elements.

One or more embodiments have been described with reference to flowchart illustrations and/or block diagrams of methods, apparatus (systems) and computer program products according to one or more embodiments. Each block of such illustrations/diagrams, or combinations thereof, can be implemented by computer program instructions. The computer program instructions when provided to a processor produce a machine, such that the instructions, which execute via the processor create means for implementing the functions/operations specified in the flowchart and/or block diagram. Each block in the flowchart/block diagrams may represent a hardware and/or software module or logic, implementing one or more embodiments. In alternative implementations, the functions noted in the blocks may occur out of the order noted in the figures, concurrently, etc.

The terms "computer program medium," "computer usable medium," "computer readable medium", and "computer program product," are used to generally refer to media such as main memory, secondary memory, removable storage drive, a hard disk installed in hard disk drive. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Computer program instructions may be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Computer program instructions representing the block diagram and/or flowcharts herein may be loaded onto a computer, programmable data processing apparatus, or processing devices to cause a series of operations performed thereon to produce a computer implemented process. Computer programs (i.e., computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system. A computer program product comprises a tangible storage medium readable by a computer system and storing instructions for execution by the computer system for performing a method of one or more embodiments.

Though the embodiments have been described with reference to certain versions thereof; however, other versions are possible. Therefore, the spirit and scope of the appended claims should not be limited to the description of the preferred versions contained herein.

What is claimed is:

1. A method for pulmonary condition monitoring, comprising:

receiving initial phrase criteria comprising jitter or shimmer for selecting uttered phrases meeting the initial phrase criteria;

selecting, a phrase from an utterance of a user of an electronic device during interaction with a voice assistant of the electronic device, the selection being based on using the received initial phrase criteria and the electronic device is a personal electronic device of the user;

generating a phrase bank for the user and storing the selected phrase from the utterance in the phrase bank;

training a baseline model using the stored selected phrase from the phrase bank, wherein the selected phrase is a voice assistant command for the personal voice assistant;

capturing, by the baseline model, correlation and dependencies between one or more speech features and the stored selected phrase for one or more pulmonary conditions;

spotting the stored selected phrase from the phrase bank in an additional utterance during another interaction with the personal voice assistant;

identifying at least one speech feature that is associated with the one or more pulmonary conditions within the spotted phrase;

determining a pulmonary condition for the user based on analysis of the at least one speech feature; and updating the baseline model based on capturing the correlation and dependencies between the at least one feature and the additional utterance for the determined pulmonary condition.

2. The method of claim 1, wherein:
the at least one speech feature includes one of:
  pause within the phrase, vowel within the phrase, or a combination thereof;
the analysis of the at least one speech feature includes comparing the speech feature with a knowledge base;
the initial phrase criteria further comprising one or more of pronunciation or breathing time,
the phrase selected from the plurality of phrases is obtained from interaction with the personal voice assistant;
the selected phrase from the utterance includes at least a portion of the initial phrase criteria; and
the phrase bank captures personal voice assistant command patterns and deviations from the personal voice assistant command patterns for speech and sound events of the user with respect to each captured phrase in the phrase bank.

3. The method of claim 2, further comprising:
updating the knowledge base as a result of the analysis of the at least one speech feature; and
adjusting statistical parameters and dependencies between existing phrases stored in the phrase bank and related contextual information;
wherein jitter comprises consistency of localized periodicity for voiced sounds, and shimmer comprises consistency of localized vocal amplitude for the voiced sounds.

4. The method of claim 1, further comprising:
inserting new selected phrases and new contextual information into a personalized longitudinal model to capture additional scenarios, wherein the personalized longitudinal model captures personalized correlation and dependencies between selected phrases;
retrieving an expected position of at least one speech segment based on a knowledge base; and
determining position of the at least one speech segment based on the expected position and generate the at least one speech feature for the at least one speech segment.

5. The method of claim 2, further comprising:
identifying at least one pause within the phrase; and
determining the pulmonary condition based on analysis of pause duration and pause pattern of the at least one pause.

6. The method of claim 1, further comprising:
receiving a context accompanying the utterance; and
determining the pulmonary condition based on analysis of the at least one speech feature in view of the context, wherein the context comprises at least one of air quality information, command content information, opportunistic physiological data or a combination thereof, the command content comprises content of a search command, and the one or more speech features capture a state of the user in different contexts.

7. The method of claim 6, wherein:
the utterance is obtained passively or proactively from the user of the electronic device;
the baseline model is personalized as a result of interaction between the user of the electronic device and the personal voice assistant; and
the opportunistic physiological data is received from a smart electronic device.

8. The method of claim 7, further comprising:
detecting a cough from the utterance; and
analyzing features of the cough;
wherein determining the pulmonary condition is further based on the analysis of the features of the cough, and the baseline model outputs one or more estimated features that are provided back to the baseline model as input.

9. An electronic device comprising:
a memory storing instructions; and
at least one processor executing the instructions including a process configured to:
  receive initial phrase criteria comprising jitter or shimmer for selecting uttered phrases meeting the initial phrase criteria;
  select, a phrase from an utterance during interaction with a personal voice assistant of the electronic device, the selection based on using the received initial phrase criteria and the electronic device is a personal electronic device of a user;
  generate a phrase bank for the user and store the selected phrase from the utterance in the phrase bank;
  train a baseline model using the stored selected phrase from the phrase bank, wherein the selected phrase is a voice assistant command for the personal voice assistant;
  capture, by the baseline model, correlation and dependencies between one or more speech features and the stored selected phrase for one or more pulmonary conditions;
  spot the stored selected phrase from the phrase bank in an additional utterance during another interaction with the personal voice assistant;
  identify at least one speech feature that is associated with the one or more pulmonary conditions within the spotted phrase;
  determine a pulmonary condition for the user based on analysis of the at least one speech feature; and
  update the baseline model based on capturing the correlation and dependencies between the at least one feature and the additional utterance for the determined pulmonary condition.

10. The electronic device of claim 9, wherein:
the at least one speech feature includes one of:
  pause within the phrase, vowel within the phrase, or a combination thereof;

the analysis of the at least one speech feature includes comparing the speech feature with a knowledge base; and the initial phrase criteria further comprising one or more of pronunciation, or breathing time;

the phrase selected from the plurality of phrases is obtained from interaction with the personal voice assistant;

the selected phrase from the utterance includes at least a portion of the initial phrase criteria; and the phrase bank captures personal voice assistant command patterns and deviations from the personal voice assistant command patterns for speech and sound events of the user with respect to each captured phrase in the phrase bank.

11. The electronic device of claim 9, wherein the process is further configured to:
update the knowledge base as a result of the analysis of the at least one speech feature;
retrieve an expected position of at least one speech segment based on a knowledge base;
determine position of the at least one speech segment based on the expected position and generate the at least one speech feature for the at least one speech segment; and
adjust statistical parameters and dependencies between existing phrases stored in the phrase bank and related contextual information.

12. The electronic device of claim 10, wherein:
the process is further configured to:
identify at least one pause within the phrase;
determine the pulmonary condition based on analysis of pause duration and pause pattern of the at least one pause; and
insert new selected phrases and new contextual information into a personalized longitudinal model to capture additional scenarios, wherein the personalized longitudinal model captures personalized correlation and dependencies between selected phrases;
jitter comprises consistency of localized periodicity for voiced sounds; and
shimmer comprises consistency of localized vocal amplitude for the voiced sounds.

13. The electronic device of claim 9, wherein:
the process is further configured to:
receive a context accompanying the utterance; and
determine the pulmonary condition based on analysis of the at least one speech feature in view of the context;
wherein the context comprises at least one of air quality information, command content information, opportunistic physiological data or a combination thereof, the command content comprises content of a search command, and the one or more speech features capture a state of the user in different contexts.

14. The electronic device of claim 13, wherein:
the utterance is obtained passively or proactively from the user of the electronic device;
the baseline model is personalized as a result of interaction between the user of the electronic device and the personal voice assistant coupled to the electronic device; and
the opportunistic physiological data is received from a smart electronic device.

15. The electronic device of claim 14, wherein the process is further configured to:

detect a cough from the utterance; and
analyze features of the cough;
wherein determination of the pulmonary condition is further based on the analysis of the features of the cough, and the baseline model outputs one or more estimated features that are provided back to the baseline model as input.

16. A non-transitory processor-readable medium that includes a program that when executed by a processor performing a method comprising:
receiving initial phrase criteria comprising jitter or shimmer for selecting uttered phrases meeting the initial phrase criteria;
selecting, a phrase from an utterance of a user of an electronic device during interaction with a personal voice assistant, based on using the received initial phrase criteria, and the electronic device is a personal electronic device of the user;
generating a phrase bank for the user and storing the selected phrase from the utterance in the phrase bank;
training a baseline model using the stored selected phrase from the phrase bank, wherein the selected phrase is a voice assistant command of the personal voice assistant;
capturing, by the baseline model, correlation and dependencies between one or more speech features and the stored selected phrase for one or more pulmonary conditions;
spotting the stored selected phrase from the phrase bank in an additional utterance during another interaction with the personal voice assistant;
identifying at least one speech feature that is associated with the one or more pulmonary conditions within the spotted phrase;
determining a pulmonary condition for the user based on analysis of the at least one speech feature; and
updating the baseline model based on capturing the correlation and dependencies between the at least one feature and the additional utterance for the determined pulmonary condition.

17. The non-transitory processor-readable medium of claim 16, wherein the method further comprises:
updating the knowledge base as a result of the analysis of the at least one speech feature; and
adjusting statistical parameters and dependencies between existing phrases stored in the phrase bank and related contextual information;
wherein:
the at least one speech feature includes one of:
pause within the phrase, vowel within the phrase, or a combination thereof; and
the analysis of the at least one speech feature includes comparing the speech feature with a knowledge base;
the initial phrase criteria further comprising one or more of pronunciation, or breathing time;
the phrase selected from the plurality of phrases is obtained from interaction with the personal voice assistant;
the selected phrase includes at least a portion of the initial phrase criteria; and
the phrase bank captures personal voice assistant command patterns and deviations from the personal voice assistant command patterns for speech and sound events of the user with respect to each captured phrase in the phrase bank.

18. The non-transitory processor-readable medium of claim 17, wherein the method further comprises:

inserting new selected phrases and new contextual information into a personalized longitudinal model to capture additional scenarios, wherein the personalized longitudinal model captures personalized correlation and dependencies between selected phrases;

retrieving an expected position of at least one speech segment based on a knowledge base;

determining position of the at least one speech segment based on the expected position and generate the at least one speech feature for the at least one speech segment;

identifying at least one pause within the phrase; and determining the pulmonary condition based on analysis of pause duration and pause pattern of the at least one pause;

wherein jitter comprises consistency of localized periodicity for voiced sounds, and shimmer comprises consistency of localized vocal amplitude for the voiced sounds.

19. The non-transitory processor-readable medium of claim 16, wherein the method further comprises:

receiving a context accompanying the utterance; and determining the pulmonary condition based on analysis of the at least one speech feature in view of the context; wherein:

the utterance is obtained passively or proactively from the user of the electronic device;

the baseline model is personalized as a result of interaction between the user of the electronic device and the personal voice assistant coupled to the electronic device; and the context further comprises at least one of air quality information, command content information, opportunistic physiological data or a combination thereof, the command content comprises content of a search command, and the one or more speech features capture a state of the user in different contexts.

20. The non-transitory processor-readable medium of claim 19, wherein the method further comprises:

detecting a cough from the utterance; and analyzing features of the cough;

wherein determining the pulmonary condition is further based on the analysis of the features of the cough, the opportunistic physiological data is received from a smart electronic device, and the baseline model outputs one or more estimated features that are provided back to the baseline model as input.

* * * * *